(12) United States Patent
Robbins et al.

(10) Patent No.: US 7,022,472 B2
(45) Date of Patent: Apr. 4, 2006

(54) MUTATIONS IN HUMAN MLH1 AND HUMAN MSH2 GENES USEFUL IN DIAGNOSING COLORECTAL CANCER

(75) Inventors: David Robbins, Stevenson Ranch, CA (US); Juili Lillian Lin-Goerke, Spring City, PA (US); Jessica C. Ling, Bensalem, PA (US)

(73) Assignee: diaDexus, Inc., So. San Francisco, CA (US)

( * ) Notice: Subject to any disclaimer, the term of this patent is extended or adjusted under 35 U.S.C. 154(b) by 0 days.

(21) Appl. No.: 09/426,548

(22) Filed: Oct. 22, 1999

(65) Prior Publication Data

US 2001/0044936 A1 Nov. 22, 2001

Related U.S. Application Data

(60) Provisional application No. 60/105,180, filed on Oct. 22, 1998.

(51) Int. Cl.
*C07H 21/02* (2006.01)
*C07H 21/04* (2006.01)
*C12Q 1/68* (2006.01)

(52) U.S. Cl. ............................ 435/6; 536/23.1; 536/24.3
(58) Field of Classification Search ...................... 800/8, 800/3, 4; 536/231, 24.1, 24.33; 435/6
See application file for complete search history.

(56) References Cited

U.S. PATENT DOCUMENTS

| 5,223,610 A | 6/1993 | Burton et al. ................... 536/24 |
| 5,591,826 A | 1/1997 | de la Chapelle et al. ... 530/350 |
| 5,922,855 A * | 7/1999 | Liskay et al. ............... 536/23.5 |

FOREIGN PATENT DOCUMENTS

WO    WO 95/20678    3/1995

OTHER PUBLICATIONS

Reitmair et al. Nature Genetics 11(1):64–70, Sep. 1995.*
Farrington et al. American Journal of Human Genetics 63(3):749–59, Sep. 1998.*
Weber et al. Cancer Research 57(17):3798–803, Sep. 1997.*
Brenner et al., "Mutation in the DNA mismatch repair gene is associated with hereditary non–polyposis colon cancer", 1994 *Nature* 368,258–261.
Burke et al., "Recommendations for Follow–up Care of Individuals With an Inherited Predisposition to Cancer", 1997 *J. Am. Med. Assoc.* 277(11) 915–919.
Dunlop et al., "Screening for people with a family history of colorectal cancer", 1997 314: 1779–1790.
Dutton et al., "Simultaneous Detection of Multiple Single–Base Alleles at a Polymorphic Site", 1999 *Biotechniques* 11: 700–702.

Fishel et al., "The Human Mutator Gene Homolog MSH2 and Its Association with Hereditary Nonpolyposis Colon Cancer", 1993 *Cell* 75; 1027–1038.
Frohman et al., "Cut, Paste and Save: New Approaches to Altering Specific Genes in Mice", 1989 *Cell* 56; 145–147.
Giardiello et al., "The Use and Interpretation of Commercial APC Gene Testing for Familial Adenomatous Polyposis", 1997 *New Engl. J. Med.* 336: 823–827.
Han et al., Genomic structure of human mismatch repair gene, hMLH1, and its mutation analysis in patients with hereditary non–polyposis colorectal cancer (HNPCC) 1995 *Human Mol. Genet.* 4(2) 237–242.
Kohler et al., "Continuous cultures of fused cells secreting antibody of predefined specificity", 1975 *Nature* 256; 495–497.
Kolodner et al., "Structure of the Human MLH1 Locus and Analysis of a Large Hereditary Nonpolyposis Colorectal Carcinoma Kindred for mlhl Mutations", 1995 *Cancer Research* 55; 242–248.
Kolodner et al., "Structure of the Human MSH2 Locus and Analysis of Two Muir–Torre Kindreds for msh2 Mutations", 1994 *Genomics* 24; 516–526.
Leach et al., "Mutations of a mutS Homolog in Hereditary Nonpolyposis Colorectal Cancer", 1993 *Cell* 75;1215–1225.
Liu et al., "hMSH2 Mutations in Hereditary Nonpolyposis Colorectal Cancer Kindreds" 1994 *Cancer Research* 54; 4590–4594.
Liu et al., "Analysis of mismatch repair genes in hereditary non–polyposis colorectal cancer patients", 1996 *Nature Medicine* 2; 169–174.
Liu et al., "Genetic instability occurs in the majority of young patients with colorectal cancer", 1995 *Nature Medicine* 1; 348–352.
Lynch et al., "Genetics, Natural History, Tumor Spectrum, and Pathology of Hereditary Nonpolyposis Colorectal Cancer: An Updated Review", 1993 *Gastroenterology* 104; 1535–1549.
Mary et al., "Mutational analysis of the hMSH2 gene reveals a three base pair deletion in a family predisposed to colorectal cancer development", 1994 *Human Molecular Genetics* 3(11) 2067–2069.

(Continued)

*Primary Examiner*—Joseph Woitach
(74) *Attorney, Agent, or Firm*—Licata & Tyrrell P.C.; Nathan P. Letts

(57) ABSTRACT

Variant human MLH1 and MSH2 genes are provided. Methods of using these variant genes to diagnose hereditary non-polyposis colorectal cancer (HNPCC) and/or determine a patient's susceptibility to developing HNPCC are also provided. Methods and compositions for identifying new variant MLH1 of MSH2 genes are also provided. In addition, experimental models for hereditary non-polyposis colorectal cancer comprising these variant genes are provided.

15 Claims, No Drawings

OTHER PUBLICATIONS

Newton et al., "Analysis of any point mutation in DNA. The amplification refractor mutation system (ARMS)", 1989 *Nucleic Acids Research* 17; 2503–2516.

Nicolaides et al., "Mutations of two PMS homologues in hereditary nonpolyposis colon cancer", 1994 *Nature* 371; 75–80.

Nystrom–Lahti et al., "Founding mutations and Alu–mediated recombination in hereditary colon cancer", 1995 *Nature Medicine* 1(11); 1203–1206.

Okayama et al., "Rapid, nonradioactive detection of mutations in the human genome by allele–specific amplification", 1989, *J. Lab. Clin. Med.* 1214; 105–113.

Papadopoulos et al., "Mutation of a mutL Homolog in Hereditary Colon Cancer", 1994 *Science* 263; 1625–1629.

Parker et al., "AmpliTaq DNA Polymerase, FS Dye–Terminator Sequencing: Analysis of Peak Height Patterns", 1996 *Biotechniques* 21; 694–699.

Sarkar et al., "Characterization of Polymerase Chain Reaction Amplification of Specific Alleles", 1990 *Anal. Biochem.* 186; 64–68.

Sommer et al., "A Novel Method for Detecting Point Mutations for Polymorphisms and Its Application to Population Screening for Carriers of Phenylketonuria", 1989 *Mayo Clin. Proc.* 64; 1361–1372.

Tomlinson et al., "Germline HNPCC gene variants have little influence on the risk for sporadic colorectal cancer", 1997 *J. Med. Genet.* 34; 39–42.

Vasen et al., The International Collaborative Group on Hereditary Non–Polyposis Colorectal Cancer (ICG–H-NPCC), 1991 34: 424–425.

Wijnen et al., "Seven New Mutations in hMSh2, an HNPCC Gene, Identified by Denaturing Gradient–Gel Electrophoresis", 1995 *Am. J. Hum. Genet.* 56; 1060–1066.

Wu et al., "Allele–specific enzymatic amplification of β–globin genomic DNA for diagnosis of sickle cell anemia", 1989 *Proc. Natl. Acad. Sci. USA* 86; 2757–2760.

* cited by examiner

MUTATIONS IN HUMAN MLH1 AND HUMAN MSH2 GENES USEFUL IN DIAGNOSING COLORECTAL CANCER

This application claims the benefit of U.S. provisional application Ser. No. 60/105,180, filed Oct. 22, 1998.

BACKGROUND OF THE INVENTION

Colorectal cancer (CRC) is one of the most common fatal cancers in developed countries, and the worldwide incidence is increasing. The United States and the United Kingdom are high incidence countries, with an estimated 133,500 new cases and 55,300 deaths (Parker et al. CA Cancer J. Clin. 1996 46:5–27) in the United States and 30,941 cases and approximately 17,000 deaths in the United Kingdom (HMSO UK Cancer Registry Data). The population lifetime risk is 1 in 25 in the United States and Northern Europe and thus represents a significant public health issue (Sharp et al. Cancer Registration Statistics Scotland 1981–1990, Information and Statistics Division, The National Health Service in Scotland, Edinburgh (1993)). Identification of people who are predisposed to the disease would allow targeting of effective preventative measures with the aim of reducing the considerable cancer related mortality (Burke et al. J. Am. Med. Ass'n. 1997 227:915–919).

One group of people with a very high colorectal cancer risk are those who carry germline mutations in genes that participate in DNA mismatch repair. hMSH2 (Fishel et al. Cell 1993 75:1027–1038; Leach et al. Cell 1993 75:1215–1225; U.S. Pat. No. 5,591,826) and hMLH1 (Bronner et al. Nature 1994 368:258–261; Papadopoulos et al. Science 1994 263:1625–1629; PCT Publication No. WO 95/20678, published on Aug. 3, 1995) are the two genes most commonly involved in heredity predisposition to CRC, but mutations in hPMS1 and hPMS2 also occur in a minority of cases (Nicolaides et al. Nature 1994 371:75–80). Such mutations are usually associated with marked familial aggregation of colorectal, uterine and other cancers constituting the clinically defined autosomal dominant syndrome of hereditary non-polyposis colorectal cancer (HNPCC) (Lynch et al. Gastroenterology 1993 104:1535–1549; Liu et al. Nature Med. 1996 2:169–174; Wijnen et al. Am. J. Hum. Genet. 1995 56:1060–1066; Mary et al. Hum. Mol. Genet. 1994 3:2067–2069; Nystrom-Lahti et al. Nature Med. 1995 1:1203–1206). However, an appreciable proportion of patients who have early onset colorectal cancer but who do not fulfill pragmatic criteria for HNPCC (Vasen et al. Dis. Colon Rectum 1991 34:424–425) also carry mismatch repair gene mutations (Liu et al. Nature Med. 1995 2:169–174; Dunlop et al. Br. Med. J. 1997 314:1779–1780). Thus, restricting genetic testing to individuals from families fulfilling HNPCC criteria is likely to exclude a significant fraction of gene carriers in the general population. However, screening unselected patients with sporadic cancer represents an enormous workload and may provide a very low yield of mutation carriers (Liu et al. Nat. Med. 1995 1:348–352; Tomlinson et al. J. Med. Genet. 1997 34:39–42).

It is clear that issues concerning indications for genetic testing and interpretation of results are critical in hereditary cancer syndromes (Giardiello et al. N. Engl. J. Med. 1997 336: 823–827).

Using a population-based approach, factors indicative of the likelihood of identifying patients with mismatch repair gene mutations were investigated. Improved approaches to mutation detection and the prevalence of detectable mismatch repair gene alterations in various screened groups who were not selected on the basis of family history were also determined.

SUMMARY OF THE INVENTION

An object of the present invention is to provide novel, variant hMLH1 sequences.

Another object of the present invention is to provide novel, variant hMSH2 sequences.

Another object of the present invention is to provide a method of diagnosing hereditary non-polyposis colorectal cancer in a patient or determining a patient's susceptibility to developing hereditary non-polyposis colorectal cancer via detection of novel variant hMLH1 or hMSH2 sequences or the exonic or intronic sequences of the hMLH1 and hMSH2 genes.

Another object of this invention is to provide methods and compositions for identifying new variants of hMLH1 and hMSH2 genes.

Yet another object of the present invention is to provide experimental models of hereditary non-polyposis colorectal cancer.

DETAILED DESCRIPTION OF THE INVENTION

To better elucidate the structure of human MLH1 and human MSH2 genes and to determine possible sites of alternative splicing, the genes were cloned and sequenced and PCR was used to determine alternate splice products (variants) and exon/intron boundaries. Elucidation of intron/exon boundary sequences revealed that hMLH1 is encoded by 19 coding exons. The hMLH1 gene sequence was determined by PCR.

The intron/exon structure of the hMLH1 is shown below. Positions of introns that interrupt the hMLH1 cDNA are shown. Exonic sequence is presented in upper case and intronic sequence in lower case letters. Exons are numbered from the 5' end of the cDNA sequence.

hMLH1 Exon 1
aggcactgaggtgattggc (SEQ ID NO:1)
tgaaggcacttccgttgagcatctagacgtttccttggctcttctggcgccaaa (SEQ ID NO:2)
ATGTCGTTCGTGGCAGGGGTTATTCG-GCGGCTGGACGAGACAGTGGTGAACCG-CATCGCGGCGGGGGAAGTTATCCAGCG-GCCAGCTAATGCTATCAAAGAGATGATTGAGAACTG (SEQ ID NO:3)
gtacggagggagtcgagccgg (SEQ ID NO:4)
gctcacttaagggctacga (SEQ ID NO:5)
cttaacgg (SEQ ID NO:6)
hMLH1 Exon 2
aatatgtacattagagtagttg (SEQ ID NO:7)
cagactgataaattattttctgtttgatttgccag (SEQ ID NO:8)
TTTAGATGCAAAATCCACAAGTAT-TCAAGTGATTGTTAAAGAGGGAGGCCT-GAAGTTGATTCAGATCCAAGACAATG-GCACCGGGATCAGG (SEQ ID NO:9)
gtaagtaaaacctcaaagtagcaggatgtttgtgcgcttcatggaa (SEQ ID NO:10)
gagtcaggacctttctctg (SEQ ID NO:11)
hMLH1 Exon 3
agagatttggaaaatgagtaac (SEQ ID NO:12)
atgattatttactcatcttttggtatctaacag (SEQ ID NO:13)
AAAGAAGATCTGGATATTGTATGT-GAAAGGTTCACTACTAGTAAACTG-CAGTCCTTTGAGGATTTAGCCAG-TATTTCTACCTATGGCTTTCGAGGTGAG (SEQ ID NO:14)

gtaagctaaagattcaagaaatgtgtaaaatat (SEQ ID NO:15)
cctcctgtgatgacattgt (SEQ ID NO:16)
c
hMLH1 Exon 4
aacctttcccttggtgagg (SEQ ID NO:17)
tgacagtgggtgacccagcagtgagttttctttcagtctattttcttttcttcttag (SEQ ID NO:18)
GCTTTGGCCAGCATAAGCCATGTGGCT-
CATGTTACTATTACAACGAAAACAGCT-
GATGGAAAGTGTGCATACAG (SEQ ID NO:19)
gtatagtgctgacttcttttactcatatatattcattctgaaatgtattttgg (SEQ ID NO:20)
gcctaggtctcagagtaatc (SEQ ID NO:21)
hMLH1 Exon 5
ttgatat (SEQ ID NO: 22)
gattttctcttttcccttggg (SEQ ID NO:23)
attagtatctatctctctactggatattaatttgttatattttctcattag (SEQ ID NO: 24)
AGCAAGTTACTCAGATGGAAAACT-
GAAAGCCCCTCCTAAACCATGTGCTG-
GCAATCAAGGGACCCAGATCACG (SEQ ID NO: 25)
gtaagaatggtacatgggaca (SEQ ID NO:26)
gtaaattgttgaagcttgtttg (SEQ ID NO:27)
hMLH1 Exon 6
gggttttattttcaagtacttctatg (SEQ ID NO: 28)
aatttacaagaaaaatcaatcttctgttcag (SEQ ID NO: 29)
GTGGAGGACCTTTTTTACAACATAGC-
CACGAGGAGAAAAGCTTTAAAAAATC-
CAAGTGAAGAATATGGGAAAATTTTG-
GAAGTTGTTGGCAG (SEQ ID NO:30)
gtacagtccaaaatctgg-
gagtgggtctctgagatttgtcatcaaagtaatgtgttctagt (SEQ ID NO:31)
gctcatacattgaacagttgctgagc (SEQ ID NO:32)
hMLH1 Exon 7
ctagtgtgtgttttggc (SEQ ID NO:33)
aactcttttcttactctttgttttctttccag (SEQ ID NO:34)
GTATTCAGTACACAATGCAGGCATT-
AGTTTCTCAGTTAAAAAA (SEQ ID NO:35)
gtaagttcttggtttatggggatg-
gttttgttttatgaaaagaaaaaaggggattttttaatagtttgct (SEQ ID NO:36)
ggtggagataaggttatg (SEQ ID NO:37)
hMLH1 Exon 8
ctcagccatgagacaataaatcc (SEQ ID NO:38)
ttgtgtcttctgctgtttgtttatcag (SEQ ID NO:39)
CAAGGAGAGACAGTAGCTGATGTTAGGA-
CACTACCCAATGCCTCAACCGTGGA-
CAATATTCGCTCCATCTTTGGAAATGCT-
GTTAGTCG (SEQ ID NO:40)
gtatgtcgataacctatataaaaaaatcttttacatttattatcttggtttatcatt (SEQ ID NO:41)
ccatcacattatttgggaacc (SEQ ID NO: 42)
hMLH1 Exon 9
caaaagcttcagaatctc (SEQ ID NO: 43)
ttttctaatag (SEQ ID NO:44)
AGAACTGATAGAAATTGGATGTGAG-
GATAAAACCCTAGCCTTCAAAATGAATG-
GTTACATATCCAATGCAAACTACTCAGT-
GAAGAAGTGCATCTTCTTACTCTTCATCAACC (SEQ ID NO:45)
gtaagttaaaaagaaccacatgggaaat (SEQ ID NO:46)
ccactcacaggaaacacccacag (SEQ ID NO:47)
hMLH1 Exon 10
catgactttgtgtgaatgtacacc (SEQ ID NO: 48)
tgtgacctcacccctcaggacagttttgaactggttgcttctttttattgtttag (SEQ ID NO:49)
ATCGTCTGGTAGAATCAACTTCCT-
TGAGAAAAGCCATAGAAACAGTGTATG-
CAGCCTATTTGCCCAAAAACACACAC-
CCATTCCTGTACCTCAG (SEQ ID NO:50)
gtaatgtagcaccaaactcctcaaccaagactcacaaggaa (SEQ ID NO:51)
cagatgttctatcaggctctcctc (SEQ ID NO: 52)
hMLH1 Exon 11
gggcttttctccccctccc (SEQ ID NO:53)
actatctaaggtaattgttctctcttattttcctgacag (SEQ ID NO: 54)
TTTAGAAATCAGTCCCCAGAATGTGGAT-
GTTAATGTGCACCCCACAAAGCAT-
GAAGTTCACTTCCTGCACGAGGAGAG-
CATCCTGGAGCGGGTGCAGCAGCACATCGAGAG
CAAGCTCCTGGGCTCCAATTCCTCCAG-
GATGTACTTCACCCAG (SEQ ID NO:55)
gtcagggcgcttctcatccagctact-
tctctggggcctttgaaatgtgcccggccaga (SEQ ID NO:56)
cgtgagagcccagatttt (SEQ ID NO:57)
hMLH1 Exon 12
aattatacctcatactagc (SEQ ID NO:58)
ttctttcttagtactgctccatttggg-
gacctgtatatctatacttcttattct-
gagtctctccactatatatatatatatatatatattttttttttttttttttttaatacag (SEQ ID NO:59)
ACTTTGCTACCAGGACTTGCTGGC-
CCCTCTGGGGAGATGGTTAAATCCACAA-
CAAGTCTGACCTCGTCTTCTACTTCTG-
GAAGTAGTGATAAGGTCTATGCCCACCAGATGGT
TCGTACAGATTCCCGGGAACAGAAGCT-
TGATGCATTTCTGCAGCCTCTGAG-
CAAACCCCTGTCCAGTCAGCCCCCAGGC-
CATTGTCACAGAGGATAAGCAGATATTTCTAGT
GGCAGGGCTAGGCAGCAAGATGAG-
GAGATGCTTGAACTCCCAGCCCCTGCT-
GAAGTGGCTGCCAAAAATCAGAGCTTG-
GAGGGGGATACAACAAAGGGGACTTCAGAAATG
TCAGAGAAGAGAGGACCTACTTCCAG-
CAACCCCAG (SEQ ID NO:60)
gtatggccttttgggaaaagtacagccta (SEQ ID NO:61)
cctcctttattctgtaataaaac (SEQ ID NO:62)
hMLH1 Exon 13
tgcaacccacaaaatttggc (SEQ ID NO:63)
taagtttaaaaacaagaataataatgatctgcacttccttttcttcattgcag (SEQ ID NO:64)
AAAGAGACATCGGGAAGATTCTGATGTG-
GAAATGGTGGAAGATGATTCCCGAAAG-
GAAATGACTGCAGCTTGTACCCCCCG-
GAGAAGGATCATTAACCTCACTAGTGTTTTGAGT
CTCCAGGAAGAAATTAATGAGCAGGGA-
CATGAGG (SEQ ID NO:65)
gtacgtaaacgctgtggcctgcctgggatgcatagggcctcaactgccaa (SEQ ID NO: 66)
ggttttggaaatggagaaag (SEQ ID NO:67)
hMLH1 Exon 14
tggtgtctctagttctgg (SEQ ID NO: 68)
tgcctggtgctttggtcaat-
gaagtgggggttggtaggattctattact-
tacctgttttttggttttattttttgttttgcag (SEQ ID NO:69)
TTCTCCGGGAGATGTTGCATAACCACTC-
CTTCGTGGGCTGTGTGAATCCT-
CAGTGGGCCTTGGCACAGCATCAAAC-
CAAGTTATACCTTCTCAACACCACCAAGCTTAG (SEQ ID NO:70)
gtaaatcagctgagtgtgtgaacaa (SEQ ID NO:71)
gcagagctactacaacaatg (SEQ ID NO: 72)

hMLH1 Exon 15
cccatttgtcccaactgg (SEQ ID NO:73)
ttgtatctcaagcatgaattcagcttttccttaaagtcacttcattttattttcag (SEQ ID NO:74)
TGAAGAACTGTTCTACCAGATACTCATT-
TATGATTTTGCCAATTTTGGTGTTCT-
CAGGTTATCG (SEQ ID NO:75)
gtaagtttagatccttttcactt (SEQ ID NO:76)
ctgacatttcaactgaccg (SEQ ID NO:77)
hMLH1 Exon 16
catttggatgctccgttaaagc (SEQ ID NO:78)
ttgctccttcatgttcttgcttcttcctag (SEQ ID NO:79)
GAGCCAGCACCGCTCTTTGACCTTGC-
CATGCTTGCCTTAGATAGTCCA-
GAGAGTGGCTGGACAGAGGAAGATGGTC-
CCAAAGAAGGACTTGCTGAATACATTGTTGAGT
TTCTGAAGAAGAAGGCTGAGATGCTTG-
CAGACTATTTCTCTTTGGAAATTGATGAG (SEQ ID NO:80)
gtgtgacagccattcttatacttctgttgtattctc (SEQ ID NO:81)
caaataaaatttccagccgggtg (SEQ ID NO:82)
hMLH1 Exon 17
ggaaaggcactggagaaatggg (SEQ ID NO:83)
atttgtttaaactatgacagcattatttcttgttcccttgtccttttcctgcaagcag (SEQ ID NO:84)
GAAGGGAACCTGATTGGATTACCCT-
TCTGATTGACAACTATGTGCCCCCTTTG-
GAGGGACTGCCTATCTTCATTCTTCGAC-
TAGCCACTGAG (SEQ ID NO:85)
gtcagtgatcaagcagatactaagcattt (SEQ ID NO:86)
cggtacatgcatgtgctggaggg (SEQ ID NO:87)
hMLH1 Exon 18
taagtagtctgtgatctccg (SEQ ID NO:88)
tttagaatgagaatgtttaaattcgtacctattttgaggtattgaatttctttggaccag (SEQ ID NO:89)
GTGAATTGGGACGAAGAAAAGGAAT-
GTTTTGAAAGCCTCAGTAAAGAATGCGC-
TATGTTCTATTCCATCCGGAAGCAGTA-
CATATCTGAGGAGTCGACCCTCTCAGGCCAGCAG (SEQ ID NO:90)
gtacagtggtgatgcacactggcaccccaggacta (SEQ ID NO:91)
gacaggacctcatacat (SEQ ID NO:92)
hMLH1 Exon 19
gacaccagtgtatgttgg (SEQ ID NO:93)
gatgcaaacagggaggcttatgacatctaatgtgttttccag (SEQ ID NO:94)
AGTGAAGTGCCTGGCTCCATTC-
CAAACTCCTGGAAGTGGACTGTGGAACA-
CATTGTCTATAAAGCCTTGCGCTCACA-
CATTCTGCCTCCTAAACATTTCACAGAAGATGGA
AATATCCTGCAGCTTGCTAACCTGCCT-
GATCTATAC
AAAGTCTTTGAGAGGTGTTAA (SEQ ID NO:95)
atatggttatttatgcactgt (SEQ ID NO:96)
gggatgtgttcttctttctc (SEQ ID NO:97)
tgtattccgatacaaagtgttgtat-
caaagtgtgatatacaaagtgtaccaacataagtg (SEQ ID NO:98)

Elucidation of intron/exon boundary sequences revealed that hMSH2 is encoded by 16 coding exons. The hMSH2 gene sequence was determined by PCR.

The intron/exon structure of the hMSH2 is shown below. Positions of introns that interrupt the hMSH2 cDNA are shown. Exonic sequence is presented in upper case and intronic sequence in lower case letters. Exons are numbered from the 5' end of the cDNA sequence.

hMSH2 Exon 1
ggcgggaaacagcttagtgggtgtggggtcg (SEQ ID NO:99)
cgcattttcttcaaccagga (SEQ ID NO:100)
ggtgaggaggtttcgac (SEQ ID NO:101)
ATGGCGGTGCAGCCGAAGGAGACGCTG-
CAGTTGGAGAGCGCGGCCGAGGTCGGCT-
TCGTGCGCTTCTTTCAGGGCATGCCG-
GAGAAGCCGACCACCACAGTGCGCCTTTTCGAC
CGGGGCGACTTCTATACGGCGCACGGC-
GAGGACGCGCTGCTGGCCGCCCGGGAG-
GTGTTCAAGACCCAGGGGGTGATCAAG-
TACATGGGGCCGGCAG (SEQ ID NO:102)
gtgagggcggggac (SEQ ID NO:103)
ggcgcgtgctggggagg (SEQ ID NO:104)
gac
hMSH2 Exon 2
gaa
gtccagctaatacagtgcttg (SEQ ID NO:105)
aacatgtaatatctcaaatctgtaatgtacttttttttttttaag (SEQ ID NO:106)
GAGCAAAGAATCTGCAGAGTGTTGTGCT-
TAGTAAAATGAATTTTGAATCTTTTG-
TAAAAGATCTTCTTCTGGTTCGTCAG-
TATAGAGTTGAAGTTTATAAGAATAGAGCTGGAA
ATAAGGCATCCAAGGAGAATGATTGG-
TATTTGGCATATAAG (SEQ ID NO:107)
gtaattatcttcctttttaatttacttattttt (SEQ ID NO:108)
ttaagagtagaaaaataaaaatgtg (SEQ ID NO:109)
aag
hMSH2 Exon 3
ATTAATAAGGtCATAGAGTTTGGATTTTTCCtTTTtgc (SEQ ID NO:110)
ttataaaattttaaagtatgttcaag (SEQ ID NO:111)
agtttgttaaattttaaaatttatttttacttag (SEQ ID NO:112)
GCTTCTCCTGGCAATCTCTCT-
CAGTTTGAAGACATTCTCTTTGGTAA-
CAATGATATGTCAGCTTCCATTGGTGT-
TGTGGGTGTTAAAATGTCCGCAGTTGATGGCCA
GAGACAGGTTGGAGTTGGGTATGTGGAT-
TCCATACAGAGGAAACTAGGACTGTGT-
GAATTCCCTGATAATGATCAGTTCTC-
CAATCTTGAGGCTCTCCTCATCCAGATTGGACCA
AAGGAATGTGTTTTACCCGGAG-
GAGAGACTGCTGGAGACATGGGGAAACT-
GAGACAG (SEQ ID NO:113)
gtaagcaaattgagtctagtgat (SEQ ID NO:114)
agaggagattccaggcctaggaaag (SEQ ID NO:115)
gc
TCTTTAATTGACATGATACTG (SEQ ID NO:116)
hMSH2 Exon 4
ttca
tttttgcttttcttattccttttc (SEQ ID NO:117)
tcatagtagtttaaactatttctttcaaaatag (SEQ ID NO:118)
ATAATTCAAAGAGGAGGAATTCTGATCA-
CAGAAAGARAAAAAGCTGACTTTTCCA-
CAAAAGACATTTATCAGGACCTCAACCG-
GTTGTTGAAAGGCAAAAAGGGAGAGCAGATGAA
TAGTGCTGTATTGCCAGAAATGGAGAATCAG (SEQ ID NO:119)
gtacatggattataaatgtgaatta-
caatatatataatgtaaatatg-
taatatataataataatatgtaaactatagtgactttt (SEQ ID NO:120)
ttagaaggatatttctgtca (SEQ ID NO:121)
tat
hMSH2 Exon 5
actggcacca (SEQ ID NO:122)
gtggtatagaaatcttcgattttt (SEQ ID NO:123)

aaattcttaattttag (SEQ ID NO:124)
GTTGCAGTTTCATCACTGTCTGCGG-TAATCAAGTTTTTAGAACTCTTATCA-GATGATTCCAACTTTGGA-CAGTTTGAACTGACTACTTTTGACTTCAGCCAGTATATGAAATTGGATATTGCAGCAGTCA-GAGCCCTTAACCTTTTTCAG (SEQ ID NO:125)
gtaaaaaaaaaaaaaaaaaaaaa (SEQ ID NO:126)
aaaagggttaaaaatgttgatt (SEQ ID NO:127)
gg
TTAAAAAATGTTT (SEQ ID NO:128)
t
caTTGACATATACTGAAGAAGCT (SEQ ID NO:129)
TATAAAGGAGCTAAAATATTTGGAAAT (SEQ ID NO:130)
att
ATTATACTTGGATTAGATAACTAGCTT-TAAATGGGTGTATTTT (SEQ ID NO:131)

hMSH2 Exon 6
gtt
ttcactaatgagcttgccattc (SEQ ID NO:132)
ttttctattttattttttgtttactag (SEQ ID NO:133)
GGTTCTGTTGAAGATACCACTGGCTCT-CAGTCTCTGGCTGCCTTGCTGAATAAGT-GTAAAACCCCTCAAGGACAAAGACTTGT-TAACCAGTGGATTAAGCAGCCTCTCATGGATAAGAACAGAATAGAGGAGAG (SEQ ID NO:134)
gtatgttattagtttatactttcgttagttttatgtaacctgca (SEQ ID NO:135)
gttacccacatgattatacc (SEQ ID NO:136)
ac hMSH2 Exon 7
ga
cttacgtgcttagttgataa (SEQ ID NO:137)
attttaattttatactaaaatattttacattaattcaagttaatttatttcag (SEQ ID NO:138)
ATTGAATTTAGTGGAAGCTTTTGTAGAA-GATGCAGAATTGAGGCAGACTTTACAA-GAAGATTTACTTCGTCGATTCCCA-GATCTTAACCGACTTGCCAAGAAGTTTCAAAGACAAGCAGCAAACTTACAAGATTGTTAC-CGACTCTAT
CAGGGTATAAATCAACTACCTAATGT-TATACAGGCTCTGGAAAAACATGAAG (SEQ ID NO:139)
gtaacaagtgattttgtttttttg (SEQ ID NO:140)
ttttccttcaactcatacaatata (SEQ ID NO:141)
tac hMSH2 Exon 8
ga
tttgtattctgtaaaatgagatcttt (SEQ ID NO:142)
ttatttgtttgttttactacttttctttag (SEQ ID NO:143)
GAAAACACCAGAAATTATTGTTG-GCAGTTTTTGTGACTCCTCTTACT-GATCTTCGTTCTGACTTCTC-CAAGTTTCAGGAAATGATAGAAACAACTTTAGATATGGATCAG (SEQ ID NO:144)
gtatgcaatatacttttaatttaag (SEQ ID NO:145)
cagtagttattttaaaaagcaaag (SEQ ID NO:146)
gcc hMSH2 Exon 9
gt
ctttacccattatttataggatt (SEQ ID NO:147)
ttgtcactttgttctgtttgcag (SEQ ID NO:148)
GTGGAAAACCATGAGAATTCCTTGTAAAAC-CTTCATTTGATCCTAATCTCAGTGAAT-TAAGAGAAATAATGAATGACTTGGAAAA-GAAGATGCAGTCAACATTAATAAGTGCAGCCAGAGATCTTG (SEQ ID NO:149)

gtaagaatgggtcattggag (SEQ ID NO:150)
gttggaataattcttttgtctat (SEQ ID NO:151)
ac hMSH2 Exon 10
gg
tagtaggtatttatggaatacttttt (SEQ ID NO:152)
tcttttcttcttgtttatcaag (SEQ ID NO:153)
GCTTGGACCCTGGCAAACAGAT-TAAACTGGATTCCAGTGCACAGTTTG-GATATTACTTTCGTGTAACCTGTAAG-GAAGAAAAAGTCCTTCGTAACAATAAAAACTTTAGTACTGTAGATATCCAGAAGAATGGTGT-TAAATTTACCAACAG (SEQ ID NO:154)
gtttgtaagtcattattatattttaaccctttatt (SEQ ID NO:155)
aattccctaaatgctctaaca (SEQ ID NO:156)
tg hMSH2 Exon 11
ca
cattgcttctagtacacattt (SEQ ID NO:157)
taatattttaataaaactgttatttcgatttgcag (SEQ ID NO:158)
CAAATTGACTTCTTTAAATGAAGAG-TATACCAAAAATAAAACAGAATATGAA-GAAGCCCAGGATGCCATTGTTAAA-GAAATTGTCAATATTTCTTCAG (SEQ ID NO:159)
gtaaacttaatagaactaa (SEQ ID NO:160)
taatgttctgaatgtcacctg (SEQ ID NO:161)
g hMSH2 Exon 12
at
tcagtattcctgtgtacattt (SEQ ID NO:162)
tctgttttattttttatacag (SEQ ID NO:163)
GCTATGTAGAACCAATGCAGACACT-CAATGATGTGTTAGCTCAGCTAGATGCT-GTTGTCAGCTTTGCTCACGTGTCAAATG-GAGCACCTGTTCCATATGTACGACCAGCCATTTTGGAGAAAGGACAAGGAAGAATTATAT-TAAAAGCATCCAGGCATGCTTGTGT-TGAAGTTCAAGATGAAATTGCATTTAT-TCCTAATGACGTATACTTTGAAAAAGATAAACAGATGTTCCACATCATTACTG (SEQ ID NO:164)
gtaaaaaacctggttt (SEQ ID NO:165)
ttgggctttgtggggtaa (SEQ ID NO:166)
cg hMSH2 Exon 13
cg
cgattaatcatcagtgtac (SEQ ID NO:167)
agtttaggactaacaatccatttattag-tagcagaagaagtttaaaatcttgctttctgatataatttgttttgtag (SEQ ID NO:168)
GCCCCAATATGGGAGGTAAATCAA-CATATATTCGACAAACTGGGGTGATAG-TACTCATGGCCCAAATTGGGTGTTTTGT-GCCATGTGAGTCAGCAGAAGTGTCCATTGTGGACTGCATCTTAGCCCGAGTAGGGGCTGGT-GACAGTCAATTGAAAGGAGTCTCCACGT-TCATGGCTGAAATGTTGGAAACTGCTTC-TATCCTCAG (SEQ ID NO:169)
gtaagtgcatctcctagtcccctt (SEQ ID NO:170)
gaagatagaaatgtatgtctctg (SEQ ID NO:171)
tcc hMSH2 Exon 14
ta
ccacatttttatgtgatgggaa (SEQ ID NO:172)
attcatgtaattatgtgcttcag (SEQ ID NO:173)
GTCTGCAACCAAAGATTCATTAATAAT-CATAGATGAATTGGGAAGAGGAACTTC-TACCTACGATGGATTTGGGTTAG- CATGGGCTATATCAGAATACATTGCAACAAAGAT
TGGTGCTTTTTGCATGTTTGCAAC-
CCATTTTCATGAACTTACTGCCTTGGC-
CAATCAGATACCAACTGTTAATAATCTA-
CATGTCACAGCACTCACCACTGAAGAGACCTTA
ACTATGCTTTATCAGGTGAAGAAAG (SEQ ID
NO:174)
gtatgtactattggagtactctaaattcagaacttg
gtaatgggaaacttactacc (SEQ ID NO:175)
cc hMSH2 Exon 15 ct
cttctcatgctgtcccctc (SEQ ID NO:176)
acgcttccccaaatttcttatag (SEQ ID NO:177)
GTGTCTGTGATCAAAGTTTTGGGAT-
TCATGTTGCAGAGCTTGCTAATTTC-
CCTAAGCATGTAATAGAGTGTGCTAAA-
CAGAAAGCCCTGGAACTTGAGGAGTTTCAGTATA
TTGGAGAATCGCAAGGATATGATAT-
CATGGAACCAGCAGCAAAGAAGTGC-
TATCTGGAAAGAGAG (SEQ ID NO:178)
gtttgtcagtttgttt (SEQ ID NO:179)
catagtttaacttagcttctc (SEQ ID NO:180)
tat hMSH2 Exon 16 ta
attactcatgggacattcaca (SEQ ID NO:181)
tgtgtttcag (SEQ ID NO:182)
CAAGGTGAAAAAATTATTCAGGAGTTC-
CTGTCCAAGGTGAAACAAATGCCCTT-
TACTGAAATGTCAGAAGAAAACATCA-
CAATAAAGTTAAAACAGCTAAAAGCTGAAGTAA
TAGCAAAGAATAATAGCTTTGTAAAT-
GAAATCATTTCACGAATAAAAGTTACTACGTGA
(SEQ ID NO:183)
aaa
atcccagtaatggaatgaag (SEQ ID NO:184)
gta hMLH1 and hMSH2 genes were sequenced in 50 cancer patients (age of onset <30) and 26 random anonymous donors. Initial genomic sequencing detected 12 germline mutations in 12 patients (24%). Five mutations were found in hMLH1, and 7 in hMSH2. Using a combination of genomic sequencing and in vitro synthesized-protein-truncation assay (IVSP), a total of 15 germ-line mutations were identified. The mutations are described in Table 1.

TABLE 1

Pathogenic hMLH1 and hMSH2 Mutations Identified in Young Colorectal Cancer Probands

| Gene and Patient | Mutation | Nucleotide Change | Effect on Coding Sequence | Location |
|---|---|---|---|---|
| hMLH1: | | | | |
| 329 | 616delAAG | Deletion of AAG at 1846–1848 | Deletion of Lys616 | Exon 16 |
| 533 | IVS8-3delTA | Deletion of TA at 677-3 | Splice mutation | IVS 8 |
| 696 | K618A | AA→GC at 1852–1853 | Lys→Ala at 618 | Exon 16 |
| 804 | R659X | C→T at 1975 | Arg→Stop at 659 | Exon 17 |
| 815 | IVS1 + 1G→A | G→A at 116 + 1 | Splice mutation | IVS 1 |
| 817 | del exon 13 | Deletion of ~3 kb involving IVS 12 through exon 13 to IVS 13 | Deletion of codons 470–520 (exon 13) | IVS 12–13, exon 13 |
| 889 | not identified | | Truncation of IVSF | Exons 12–19 |
| hMSH2: | | | | |
| 528 | R406X | C→T at 1216 | Arg→Stop at 406 | Exon 7 |
| 579 | H639Y IVS13-1G→T | C→T at 1915 G→T at 2211 | Double mutation results in deletion of codons 588–820 (exons 12–14) | Exon 12, IVS 13 |
| 814 | Q601X | C→T at 1801 | Gln→Stop at 601 | Exon 12 |
| 818 | Q252X | C→T at 754 | Gln→Stop at 252 | Exon 4 |
| 825 | delCTGT | Deletion of CTGT at 808–811 | Deletion of codons 265–314 (exon 5) | Exon 5 |
| 830 | R680X | C→T at 2038 | Arg→Stop at 680 | Exon 13 |
| 1157 | M1L | A→T at 1 | New initiation at codon 26 | Exon 1 |

"IVS" means intervening sequence.

Two of the mutations identified in Table 1 for hMLH1 and three of the mutations identified in Table 1 for hMSH2 are believed to be new. For hMLH1, these include: the splice mutation IVS1+1G-A in patient 815, also referred to herein as "hMLH1 mutant 1"; and deletion of exon 13 in patient 817, also referred to herein as "hMLH1 mutant 2". For hMSH2, these include the double mutation H639Y IVS13-1G-T leading to deletion of codons 588–820 in patient 579, also referred to herein as "hMSH2 mutant 1", mutation R680X in patient 830 which comprises a nucleotide change from C to T at position 2038 in Exon 13 and results in a stop codon at position 680 of the coding sequence, also referred to herein as "hMSH2 mutant 2"; and mutation M1L in patient 1157 which comprises a nucleotide change from A to T at position 1 resulting in a new initiation at codon 26, also referred to herein as "hMSH2 mutant 3". Detection of these genetic mutations is useful in diagnosing HNPCC in a patient and determining susceptibility of a patient for developing HNPCC.

There are several methodologies available from recombinant DNA technology which may be used for detecting these new variants and identifying additional genetic mutations responsible for colon cancer. The identification of intronic sequences of hMLH1 and hMSH2 provided herein is particularly useful for design of intronic such as those exemplified in SEQ ID NO:1, 5, 7, 11, 12, 16, 17, 21, 23, 27, 28, 32, 33, 37, 38, 42, 43, 47, 48, 52, 53, 57, 58, 62, 63, 67, 68, 72, 73, 77, 78, 82, 83, 87, 88, 92, 93, 97, 100, 104, 105, 109, 111, 115, 117, 121, 123, 121, 123, 127, 129, 132, 136, 137, 141, 142, 146, 147, 151, 152, 156, 157, 161, 162, 166, 167, 171, 172, 175, 176, 180, 181 and 184 for use in identifying mutants in the splice donor or acceptor sites of the hMLH1 or hMSH2 gene. Examples of methodologies useful in detecting and identifying new variants of these genes include, but are not limited to, direct probing, ligase chain reaction (LCR) and polymerase chain reaction (PCR) methodology.

Detection of variants or mutants using direct probing involves the use of oligonucleotide probes which may be prepared synthetically or by nick translation. In a preferred embodiment, the probes are complementary to at least a portion of the variant hMLH1 or hMSH2 genes identified herein. The DNA probes may be suitably labeled using, for example, a radiolabel, enzyme label, fluorescent label, or biotin-avidin label, for subsequent visualization in for example a Southern blot hybridization procedure. The labeled probe is reacted with a sample of DNA from a patients suspected of having HNPCC bound to nitrocellulose or Nylon 66 substrate. The areas that carry DNA sequences complementary to the labeled DNA probe become labeled themselves as a consequence of the reannealing reaction. The areas of the filter that exhibit such labeling may then be visualized, for example, by autoradiography.

Alternative probe techniques, such as ligase chain reaction (LCR) involve the use of a mismatch probe, i.e., probes which have full complementarity with the target except at the point of the mutation or variation. The target sequence is then allowed to hybridize both with the oligonucleotides having full complementarity, i.e., oligonucleotides complementary to the hMLH1 or hMSH2 variants of the present invention, and oligonucleotides containing a mismatch under conditions which will distinguish between the two. By manipulating the reaction conditions, it is possible to obtain hybridization only where there is full complementarity. If a mismatch is present, then there is significantly reduced hybridization.

The polymerase chain reaction (PCR) is a technique that amplifies specific DNA sequences. Repeated cycles of denaturation, primer annealing and extension carried out with a heat stable enzyme Taq polymerase leads to exponential increases in the concentration of desired DNA sequences.

Given the knowledge of nucleotide sequences encoding the hMLH1 and hMSH2 genes, it is possible to prepare synthetic oligonucleotides complementary to the sequences which flank the DNA of interest. Each oligonucleotide is complementary to one of the two strands. The DNA is then denatured at high temperatures (e.g., 95° C.) and then reannealed in the presence of a large molar excess of oligonucleotides. The oligonucleotides, oriented with their 3' ends pointing towards each other, hybridize to opposite strands of the target sequence and prime enzymatic extension along the nucleic acid template in the presence of the four deoxyribonucleotide triphosphates. The end product is then denatured again for another cycle. After this three-step cycle has been repeated several times, amplification of a DNA segment by more than one million fold can be achieved. The resulting DNA may then be directly sequenced in order to locate any genetic alterations. Alternatively, the identified hMLH1 and hMSH2 variants of the present invention make it possible to prepare oligonucleotides that will only bind to altered DNA, so that PCR will only result in the multiplication of the DNA if the mutation is present. Following PCR, allele-specific oligonucleotide hybridization may be used to detect the colon cancer point mutation.

Alternatively, an adaptation of PCR called amplification of specific alleles (PASA) can be employed; this method uses differential amplification for rapid and reliable distinction between alleles that differ at a single base pair. Newton et al. Nucleic Acid Res. 1989 17:2503; Nichols et al. Genomics 1989 5:535; Okayama et al. J. Lab. Clin. Med. 1989 1214:105; Sarkar et al. Anal. Biochem. 1990 186:64; Sommer et al. Mayo Clin. Proc. 1989 64:1361; Wu, Proc. Nat'l Acad. Sci. USA 1989 86:2757; and Dutton et al. Biotechniques 1991 11:700. PASA involves amplification with two oligonucleotide primers such that one is allele specific. The desired allele is efficiently amplified, while the other allele(s) is poorly amplified because it mismatches with a base at or near the 3' end of the allele specific primer. Thus, PASA or the related method PAMSA can be used to specifically amplify one or more mutant hMLH1 or hMSH2 alleles. Where such amplification is performed on genetic material obtained from a patient, it can serve as a method of detecting the presence of one or more mutant hMLH1 and/or hMSH2 alleles in a patient. PCR-induced mutation restriction analysis, often referred to as IMPA, can also be used in the detection of mutants.

Also important is the development of experimental models of HNPCC. Such models can be used to screen for agents that alter the degenerative course of HNPCC. Having identified specific mutations in the hMLH1 and hMSH2 genes as a cause of HNPCC, it is possible using genetic manipulation, to develop transgenic model systems and/or whole cell systems containing a mutated hMLH1 and/or hMSH2 gene or a portion thereof. The model systems can be used for screening drugs and evaluating the efficacy of drugs in treating HNPCC. In addition, these model systems provide a tool for defining the underlying biochemistry of hMLH1 and hMSH2 and their relationship to HNPCC, thereby providing a basis for rational drug design.

One type of cell system which can be used in the present invention can be naturally derived. For this, blood samples from an affected individual are obtained and permanently transformed into a lymphoblastoid cell line using, for example, Epstein-Barr virus. Once established, such cell lines can be grown continuously in suspension cultures and can be used in a variety of in vitro experiments to study hMLH1 and hMSH2 expression and processing. Another cell line used in these studies comprises skin fibroblasts derived from patients.

The mutated gene can also be excised for use in the creation of transgenic animals containing the mutated gene. For example, the hMLH1 and hMSH2 variants of the present invention can each be cloned and placed in a cloning vector. Examples of cloning vectors which can be used include, but are not limited to, lCharon35, cosmid, or yeast artificial chromosome. The variant hMLH1 or hMSH2 gene can then be transferred to a host nonhuman knockout animal such as a knockout mouse. As a result of the transfer, the resultant transgenic nonhuman animal will preferably express one or more of the variant hMLH1 or hMSH2 polypeptides.

Alternatively, minigenes encoding variant hMLH1 or hMSH2 polypeptides can be designed. Such minigenes may contain a cDNA sequence encoding a variant hMLH1 or hMSH2 polypeptide, preferably full-length, a combination of hMLH1 or hMSH2 exons, or a combination thereof, linked to a downstream polyadenylation signal sequence and an upstream promoter (and preferably enhancer). Such a minigene construct will, when introduced into an appropriate transgenic host, such as a mouse or rat, express a variant hMLH1 or hMSH2 polypeptide.

One approach to creating transgenic animals is to target a mutation to the desired gene by homologous recombination in an embryonic stem (ES) cell in vitro followed by microinjection of the modified ES cell line into a host blastocyst and subsequent incubation in a foster mother. Frohman et al. Cell 1989 56:145. Alternatively, the technique of microinjection of the mutated gene, or portion thereof, into a one-cell embryo followed by incubation in a foster mother can be used. Additional methods for producing transgenic animals are well known in the art.

Transgenic animals are used in the assessment of new therapeutic compositions and in carcinogenicity testing, as exemplified by U.S. Pat. No. 5,223,610. These animals are also used in the development of predictive animal models for human disease states, as exemplified in U.S. Pat. No. 5,221,778. Therefore, the novel mutations of the hMLH1 and hMSH2 genes of the present invention, which are believed to cause HNPCC, provide a useful means for developing knockout transgenic animals to assess this disease.

Site directed mutagenesis and/or gene conversion can also be used to a mutate a non human hMLH1 or hMSH2 gene allele, either endogenously or via transfection, such that the mutated gene encodes a polypeptide with an altered amino acid as described in the present invention.

In addition, antibodies to the hMLH1 or hMSH2 gene and variants thereof can be raised for use in the examination of the function of the truncated transcripts of the hMLH1 or hMSH2 gene. These antibodies can be, for example, polyclonal or monoclonal antibodies. The present invention also includes chimeric, single chain, and humanized antibodies, as well as Fab fragments, or the product of an Fab expression library. Various procedures known in the art may be used for the production of such antibodies and fragments.

Antibodies generated against the hMLH1 and hMSH2 genes of the present invention can be obtained by direct injection into an animal or by administering the gene to an animal, preferably a nonhuman. The antibody so obtained will then bind the hMLH1 or hMSH2 gene or itself. In this manner, even a fragment of the gene can be used to generate thee antibodies.

For preparation of monoclonal antibodies, any technique which provides antibodies produced by continuous cell line cultures can be used. Examples include the hybridoma technique (Kohler et al. Nature 1975 256:495–497), the trioma technique, the human B-cell hybridoma technique (Kozbor et al. Immunology Today 1983 4:72), and the EBV-hybridoma technique to produce human monoclonal antibodies (Cole et al. in *Monoclonal Antibodies and Cancer Therapy*, Alan R. Liss, Inc., 1985, pp. 77–96).

Techniques described for the production of single chain antibodies (U.S. Pat. No. 4,946,778) can be adapted to produce single chain antibodies to the hMLH1 or hMSH2 genes of this invention. Also, transgenic mice may be used to express humanized antibodies to the hMLH1 or hMSH2 genes of this invention.

The following nonlimiting examples are provided to further illustrate the present invention.

EXAMPLES

Example 1: Patients and Samples

A total of 76 subjects were studied: 50 unrelated patients diagnosed with colorectal cancer at <30 years of age and 26 anonymous donors. There were 15 male and 11 female anonymous donors who were cancer free at the time of sampling and whose mean ages was 41 years. None of the study subjects were referred specifically because of a family history of colon cancer. All cancer patients had histologically confirmed colorectal cancer.

Peripheral blood was drawn from each subject and DNA was purified from peripheral-blood leukocytes.

Example 2: Genomic Sequencing

DNA was extracted from peripheral blood using the Nucleon DNA Extraction Kit, Scotlab, Lanarkshire, U.K. or using the Puregene DNA Isolation Kit (Gentra Systems, Minneapolis, Minn.) as per the manufacturer's instructions. Each exon of hMSH2 and hMLH1 was amplified by PCR using 40 ng of genomic DNA in a volume of 50 μL. Final reaction concentrations were 1×PCR Buffer II (Perkin Elmer), 3.0 mM $MgCl_2$ (or 1.5 mM for hMSH2 exon 1), 0.2 mM dNTPs, 10 pmol of each specific oligonucleotide primer, and 1.25 units of Taq polymerase. Amplification was hot-started at 94° C. for 3 minutes, followed by 35 cycles of 94° C. for 20 seconds; 55° C. for 20 seconds; 72° C. for 40 seconds. The final reaction was extended at 72° C. for 10 minutes, followed by storage at 4° C. Cycle sequencing used the PRISM Ready Dye Terminator Cycle Sequencing kit with AmpliTaq DNA polymerase, FS (Taq-FS; Perkin Elmer/Applied Biosystems) and an Applied Biosystems DNA Sequencer model 373A or 377 (Parker et al. BioTechniques 1996 21:694–699) according to the manufacturer's instructions. DNA sequence analysis was performed using Sequencher 3.0 (Gene Codes, Ann Arbor, Mich.) software by comparing published genomic sequences of hMLH1 (Han et al. Hum. Mol. Genet. 1995 4:237–242; Kolodner et al. Cancer Res. 1995 55:242–248) and hMSH2 (Kolodner, et al. Genomics 1994 24:516–526) with that of cancer cases or of random donors.

Examples of primers used for mutations in patients 815, 830 and 1157 are as follows:

(1) Patient 815, splice error in hMLH1 exon 1:
Forward primer:
5'-TGTAAAACGACGGCCAGTCTGAGGTGATTGGCTGAAG-3' (SEQ ID NO: 185)
Reverse primer:
5'-GGAAACAGCTATGACCATGCCGTTAAGTCGTAGCCCTT-3' (SEQ ID NO: 186)

(2) Patient 830, premature stop codon in hMSH2 exon 13:
Forward primer:
5'-TGTAAAACGACGGCCAGTCGATTAATCATCAGTGTAC-3' (SEQ ID NO: 187)
Reverse primer:
5'-GGAAACAGCTATGACCATGCAGAGACATACATTTCTATCTTC-3' (SEQ ID NO: 188)

(3) Patient 1157, missense in initial ATG of hMSH2 (exon 1):
Forward primer:
5'-TGTAAAACGACGGCCAGTCGCATTTTCTTCAACCAGGA-3' (SEQ ID NO: 189)
Reverse primer:
5'-GGAAACAGCTATGACCATGCCTCCCCAGCACGCGCC-3' (SEQ ID NO: 190)

Example 2: In Vitro Synthesized-Protein-Truncation Assay (IVSP)

cDNA was generated by reverse transcription of RNA purified from lymphoblastoid cell lines from the affected index case. PCR amplification of the CDNA was used to introduce a 17-bp consensus T7 promoter sequence and a mammalian translation-initiation sequence in frame with a unique hMLH1 or hMSH2 sequence. PCR primer sequences and conditions were similar to those previously described in Example 1. Each gene was amplified in two or three overlapping segments. Resultant PCR products were used in a coupled transcription-translation reaction (Promega) incorporating 2–5 µCi of $^{35}$S-methionine. Labeled in vitro-transcribed protein products from the reaction were heat denatured and were analyzed by use of 8%, 10% and 12% SDS-PAGE gels. Gels were washed in fixative and were autoradiographed overnight at room temperature. All samples showing truncated protein products were reamplified independently, and an additional IVSP analysis was performed for conformation. For each analysis, normal control samples were run in parallel, and the wild-type full length protein was noted. In most analyses, artifactual bands were visible, presumably due to internally initiations since these were visible in samples form normal controls.

Example 3: Long Range PCR

For long range PCR of the novel mutation of hMSH2 discovered in patient 817, the GeneAmp XL PCR Kit (Perkin Elmer) was used with the following primers:

Forward primer:
5'-GGCCATTGTCACAGAGGATAAGA-3' (SEQ ID NO: 191)

Reverse primer:
5'-ACACAGCCCACGAAGGAGTG-3' (SEQ ID NO: 192)

The reaction mixture contained about 400 ng of genomic DNA in a volume of 50 µL. Final reaction concentrations were 1×PCR Buffer II (Perkin Elmer), 1.5 mM Mg(OAc)$_2$, 0.8 mM dNTPs, 40 pmol of each specific oligonucleotide primer, and 4 units of rTth DNA polymerase. Amplification was hot-started at 94° C. for 1 minute, followed by 26 cycles of 94° C. for 15 second and 68° C. for 10 minutes. The final reaction was extended at 72° C. for 10 minutes, followed by storage at 4° C.

Replicate cDNA sequencing of samples from patient 817 reproducibly demonstrated a truncation in hMSH2 due to deletion of the entire exon 13. However, extensive genomic sequencing failed to identify the mutation at the DNA level. Hence, the intronic region around exon 13 was analyzed by long range PCR to determine whether any large genomic deletion had completely removed that exon. Forward primer was in exon 12 and reverse in exon 14, giving around 15.5 kb wild type product. Using this approach, patient 817 was shown to carry a large deletion of approximately 3 kb which resulted in removal of exon 13.

Example 4: Characterization of Mutation in Patient 579

Characterization of the mutation in patient 579 was more complex. Replicate hMSH2 IVSPs for patient 579 detected a very short protein fragment, which could not be explained on the basis of the His-Tyr mutation at codon 639, identified by genomic sequencing. Accordingly, additional genomic sequencing needed to be performed which resulted in identification of the second mutation at the splice acceptor site of exon 14. Using restriction-site changes induced by each mutation, both variants were traced through the family and were shown to reside on the same allele. Extensive sequencing of the reverse transcription-PCR products revealed that this complex double mutation results in an in-frame deletion of exons 12–14, thus accounting for the very short IVSP fragment. A His-Tyr mutation at codon 639 which results in a surrogate splice donor site and a 92-bp frameshift deletion of nucleotides 1914–2006, generating a premature termination codon 17 bp downstream of the exon 13 splice acceptor site has been described previously by Leach et al. Cell 1993 75:1215–1225 and Liu et al. Cancer Res. 1994 54:4590–4594. However, the 92 bp splice mutation reported to be present in this mutation was not present in patient 579, thus confirming that the double mutation in patient 579 is distinct from that reported by Liu et al. Cancer Res. 1994 54:4590–4594.

All publications including, but not limited to, patents and patent applications, cited in this specification, are herein incorporated by reference as if each individual publication were specifically and individually indicated to be incorporated by reference herein as though fully set forth.

The above description fully discloses the invention, including preferred embodiments thereof. Modifications and improvements of the embodiments specifically disclosed herein are within the scope of the following claims. Without further elaboration, it is believed that one skilled in the art can, using the preceding description, utilize the present invention to its fullest extent. Therefore, the examples provided herein are to be construed as merely illustrative and are not a limitation of the scope of the present invention in any way. The embodiments of the invention in which an exclusive property or privilege is claimed are defined as follows.

What is claimed is:

1. A method of diagnosing hereditary non-polyposis colorectal cancer in a patient comprising:
   (a) obtaining a DNA or RNA sample from a patient; and
   (b) screening the DNA or RNA sample with an oligonucleotide probe to detect a hMLH1 mutant 1, a hMSH2 mutant 1, a hMSH2 mutant 2, or a hMSH2 mutant 3, wherein binding of the oligonucleotide probe to the DNA or RNA sample is indicative of the presence of the hMLH1 mutant 1, the hMSH2 mutant 1, the hMSH2 mutant 2, or the hMSH2 mutant 3 and hereditary non-polyposis colorectal cancer.

2. The method of claim 1 wherein the oligonucleotide probe detects a hMLH1 mutatn 1.

3. The method of claim 1 wherein the oligonucleotide probe detects a hMSH2 mutant 1.

4. The method of claim 1 wherein the oligonucleotide probe detets a hMSH2 mutant 2.

5. The method of claim 1 wherein the oligonucleotdie probe detects a hMSH2 mutant 3.

6. A method for predicting susceptibility of a patient to developing hereditary non-polyposis colorectal cancer comprising:
   (a) obtaining a DNA or RNA sample from a patient; and
   (b) screening the DNA or RNA sample with an oligonucleotide probe to detect a hMLH1 mutant 1, a hMSH2 mutant 1, a hMSH2 mutant 2, or a hMSH2 mutant 3, wherein binding of the oligonucleotide probe to the DNA or RNA sample is indicative of the presence of the hMLH1 mutant 1, the hMSH2 mutant 1, the hMSH2 mutant 2, or the hMSH2 mutant 3 and hereditary non-polyposis colorectal cancer.

7. The method of claim 6 wherein the oligonucleotide probe detects a hMLH1 mutant 1.

8. The method of claim 6 wherein the oligonucleotide probe detects a hMSH2 mutant 1.

9. The method of claim 6 wherein the oligonucleotide probe dtectes a hMSH2 mutant 2.

10. The method of claim 6 wherein the oligonucleotide probe detects a hMSH2 mutant 3.

11. An oligonucleotide probe fully complimentary to a sequence comprising a hMLH1 mutant 1, hMSH2 mutant 1, a hMSH2, or hMSH2 mutant 3 in the DNA or RNA sample.

12. The oligonucleotide probe of claim 11 wherein the oligonucleotide probe is fully complementary to a sequence comprising a hMLH1 mutant 1.

13. The Oligonucleotide probe of claim 11 wherein the oligonucleotide probe is fully complementary to a sequence comprising a hMSH2 mutant 1.

14. The oligoncleotide probe of claim 11 wherein the oligonucleotide probe is fully complementary to a sequence comprising a hMSH2 mutant 2.

15. The oligonuleotide probe of claim 11 wherein the oligonucleotide probe is fully complementary to a sequence comprising a hMSH2 mutant 3.

* * * * *

SEQUENCE LISTING

<160> NUMBER OF SEQ ID NOS: 192

<210> SEQ ID NO 1
<211> LENGTH: 19
<212> TYPE: DNA
<213> ORGANISM: Homo sapiens

<400> SEQUENCE: 1
aggcactgag gtgattggc                                          19

<210> SEQ ID NO 2
<211> LENGTH: 54
<212> TYPE: DNA
<213> ORGANISM: Homo sapiens

<400> SEQUENCE: 2
tgaaggcact tccgttgagc atctagacgt ttccttggct cttctggcgc caaa   54

```
<210> SEQ ID NO 3
<211> LENGTH: 51
<212> TYPE: DNA
<213> ORGANISM: Homo sapiens

<400> SEQUENCE: 3
ggaagttatc cagcggccag ctaatgctat caaagagatg attgagaact g          51

<210> SEQ ID NO 4
<211> LENGTH: 21
<212> TYPE: DNA
<213> ORGANISM: Homo sapiens

<400> SEQUENCE: 4
gtacggaggg agtcgagccg g                                           21

<210> SEQ ID NO 5
<211> LENGTH: 19
<212> TYPE: DNA
<213> ORGANISM: Homo sapiens

<400> SEQUENCE: 5
gctcacttaa gggctacga                                              19

<210> SEQ ID NO 6
<211> LENGTH: 8
<212> TYPE: DNA
<213> ORGANISM: Homo sapiens

<400> SEQUENCE: 6 cttaacgg                                                           8

<210> SEQ ID NO 7
<211> LENGTH: 22
<212> TYPE: DNA
<213> ORGANISM: Homo sapiens

<400> SEQUENCE: 7
aatatgtaca ttagagtagt tg                                          22

<210> SEQ ID NO 8
<211> LENGTH: 35
<212> TYPE: DNA
<213> ORGANISM: Homo sapiens

<400> SEQUENCE: 8
cagactgata aattattttc tgtttgattt gccag                            35

<210> SEQ ID NO 9
<211> LENGTH: 91
<212> TYPE: DNA
<213> ORGANISM: Homo sapiens

<400> SEQUENCE: 9
tttagatgca aaatccacaa gtattcaagt gattgttaaa gagggaggcc tgaagttgat  60
tcagatccaa gacaatggca ccgggatcag g                                91

<210> SEQ ID NO 10
<211> LENGTH: 46
<212> TYPE: DNA
<213> ORGANISM: Homo sapiens
```

```
<400> SEQUENCE: 10
gtaagtaaaa cctcaaagta gcaggatgtt tgtgcgcttc atggaa                46

<210> SEQ ID NO 11
<211> LENGTH: 19
<212> TYPE: DNA
<213> ORGANISM: Homo sapiens

<400> SEQUENCE: 11
gagtcaggac ctttctctg                                              19

<210> SEQ ID NO 12
<211> LENGTH: 22
<212> TYPE: DNA
<213> ORGANISM: Homo sapiens

<400> SEQUENCE: 12
agagatttgg aaaatgagta ac                                          22

<210> SEQ ID NO 13
<211> LENGTH: 34
<212> TYPE: DNA
<213> ORGANISM: Homo sapiens

<400> SEQUENCE: 13
atgattattt actcatcttt ttggtatcta acag                             34

<210> SEQ ID NO 14
<211> LENGTH: 99
<212> TYPE: DNA
<213> ORGANISM: Homo sapiens

<400> SEQUENCE: 14
aaagaagatc tggatattgt atgtgaaagg ttcactacta gtaaactgca gtcctttgag    60
gatttagcca gtatttctac ctatggcttt cgaggtgag                           99

<210> SEQ ID NO 15
<211> LENGTH: 33
<212> TYPE: DNA
<213> ORGANISM: Homo sapiens

<400> SEQUENCE: 15
gtaagctaaa gattcaagaa atgtgtaaaa tat                              33

<210> SEQ ID NO 16
<211> LENGTH: 19
<212> TYPE: DNA
<213> ORGANISM: Homo sapiens

<400> SEQUENCE: 16
cctcctgtga tgacattgt                                              19

<210> SEQ ID NO 17
<211> LENGTH: 20
<212> TYPE: DNA
<213> ORGANISM: Homo sapiens

<400> SEQUENCE: 17
aacctttccc tttggtgagg                                             20

<210> SEQ ID NO 18
<211> LENGTH: 59
```

```
<212> TYPE: DNA
<213> ORGANISM: Homo sapiens

<400> SEQUENCE: 18
tgacagtggg tgacccagca gtgagttttt ctttcagtct attttctttt cttccttag      59

<210> SEQ ID NO 19
<211> LENGTH: 74
<212> TYPE: DNA
<213> ORGANISM: Homo sapiens

<400> SEQUENCE: 19
gctttggcca gcataagcca tgtggctcat gttactatta caacgaaaac agctgatgga      60
aagtgtgcat acag                                                       74

<210> SEQ ID NO 20
<211> LENGTH: 53
<212> TYPE: DNA
<213> ORGANISM: Homo sapiens

<400> SEQUENCE: 20
gtatagtgct gacttctttt actcatatat attcattctg aaatgtattt tgg            53

<210> SEQ ID NO 21
<211> LENGTH: 20
<212> TYPE: DNA
<213> ORGANISM: Homo sapiens

<400> SEQUENCE: 21
gcctaggtct cagagtaatc                                                 20

<210> SEQ ID NO 22
<211> LENGTH: 7
<212> TYPE: DNA
<213> ORGANISM: Homo sapiens

<400> SEQUENCE: 22 ttgatat                                                               7

<210> SEQ ID NO 23
<211> LENGTH: 22
<212> TYPE: DNA
<213> ORGANISM: Homo sapiens

<400> SEQUENCE: 23
gattttctct tttccccttg gg                                              22

<210> SEQ ID NO 24
<211> LENGTH: 51
<212> TYPE: DNA
<213> ORGANISM: Homo sapiens

<400> SEQUENCE: 24
attagtatct atctctctac tggatattaa tttgttatat tttctcatta g              51

<210> SEQ ID NO 25
<211> LENGTH: 73
<212> TYPE: DNA
<213> ORGANISM: Homo sapiens

<400> SEQUENCE: 25
agcaagttac tcagatggaa aactgaaagc ccctcctaaa ccatgtgctg gcaatcaagg      60
```

```
gacccagatc acg                                                         73

<210> SEQ ID NO 26
<211> LENGTH: 21
<212> TYPE: DNA
<213> ORGANISM: Homo sapiens

<400> SEQUENCE: 26
gtaagaatgg tacatgggac a                                                21

<210> SEQ ID NO 27
<211> LENGTH: 23
<212> TYPE: DNA
<213> ORGANISM: Homo sapiens

<400> SEQUENCE: 27
gtaaattgtt gaagctttgt ttg                                              23

<210> SEQ ID NO 28
<211> LENGTH: 26
<212> TYPE: DNA
<213> ORGANISM: Homo sapiens

<400> SEQUENCE: 28
gggttttatt ttcaagtact tctatg                                           26

<210> SEQ ID NO 29
<211> LENGTH: 31
<212> TYPE: DNA
<213> ORGANISM: Homo sapiens

<400> SEQUENCE: 29
aatttacaag aaaaatcaat cttctgttca g                                     31

<210> SEQ ID NO 30
<211> LENGTH: 92
<212> TYPE: DNA
<213> ORGANISM: Homo sapiens

<400> SEQUENCE: 30
gtggaggacc tttttacaa catagccacg aggagaaaag ctttaaaaaa tccaagtgaa        60
gaatatggga aaattttgga agttgttggc ag                                    92

<210> SEQ ID NO 31
<211> LENGTH: 61
<212> TYPE: DNA
<213> ORGANISM: Homo sapiens

<400> SEQUENCE: 31
gtacagtcca aaatctggga gtgggtctct gagatttgtc atcaaagtaa tgtgttctag      60
t                                                                      61

<210> SEQ ID NO 32
<211> LENGTH: 26
<212> TYPE: DNA
<213> ORGANISM: Homo sapiens

<400> SEQUENCE: 32
gctcatacat tgaacagttg ctgagc                                           26

<210> SEQ ID NO 33
<211> LENGTH: 18
```

```
<212> TYPE: DNA
<213> ORGANISM: Homo sapiens

<400> SEQUENCE: 33
ctagtgtgtg tttttggc                                                 18

<210> SEQ ID NO 34
<211> LENGTH: 35
<212> TYPE: DNA
<213> ORGANISM: Homo sapiens

<400> SEQUENCE: 34
aactcttttc ttactctttt gttttctttt tccag                              35

<210> SEQ ID NO 35
<211> LENGTH: 43
<212> TYPE: DNA
<213> ORGANISM: Homo sapiens

<400> SEQUENCE: 35
gtattcagta cacaatgcag gcattagttt ctcagttaaa aaa                     43

<210> SEQ ID NO 36
<211> LENGTH: 70
<212> TYPE: DNA
<213> ORGANISM: Homo sapiens

<400> SEQUENCE: 36
gtaagttctt ggtttatggg ggatggtttt gttttatgaa agaaaaaag gggattttta    60 atagtttgct                                                          70

<210> SEQ ID NO 37
<211> LENGTH: 18
<212> TYPE: DNA
<213> ORGANISM: Homo sapiens

<400> SEQUENCE: 37
ggtggagata aggttatg                                                 18

<210> SEQ ID NO 38
<211> LENGTH: 23
<212> TYPE: DNA
<213> ORGANISM: Homo sapiens

<400> SEQUENCE: 38
ctcagccatg agacaataaa tcc                                           23

<210> SEQ ID NO 39
<211> LENGTH: 27
<212> TYPE: DNA
<213> ORGANISM: Homo sapiens

<400> SEQUENCE: 39
ttgtgtcttc tgctgtttgt ttatcag                                       27

<210> SEQ ID NO 40
<211> LENGTH: 89
<212> TYPE: DNA
<213> ORGANISM: Homo sapiens

<400> SEQUENCE: 40
caaggagaga cagtagctga tgttaggaca ctacccaatg cctcaaccgt ggacaatatt   60
```

```
cgctccatct ttggaaatgc tgttagtcg                                          89
```

<210> SEQ ID NO 41
<211> LENGTH: 57
<212> TYPE: DNA
<213> ORGANISM: Homo sapiens
<400> SEQUENCE: 41

```
gtatgtcgat aacctatata aaaaaatctt ttacatttat tatcttggtt tatcatt         57
```

<210> SEQ ID NO 42
<211> LENGTH: 21
<212> TYPE: DNA
<213> ORGANISM: Homo sapiens
<400> SEQUENCE: 42

```
ccatcacatt atttgggaac c                                                  21
```

<210> SEQ ID NO 43
<211> LENGTH: 18
<212> TYPE: DNA
<213> ORGANISM: Homo sapiens
<400> SEQUENCE: 43

```
caaaagcttc agaatctc                                                      18
```

<210> SEQ ID NO 44
<211> LENGTH: 11
<212> TYPE: DNA
<213> ORGANISM: Homo sapiens
<400> SEQUENCE: 44

```
ttttctaata g                                                             11
```

<210> SEQ ID NO 45
<211> LENGTH: 113
<212> TYPE: DNA
<213> ORGANISM: Homo sapiens
<400> SEQUENCE: 45

```
agaactgata gaaattggat gtgaggataa aaccctagcc ttcaaaatga atggttacat       60
atccaatgca aactactcag tgaagaagtg catcttctta ctcttcatca acc             113
```

<210> SEQ ID NO 46
<211> LENGTH: 28
<212> TYPE: DNA
<213> ORGANISM: Homo sapiens
<400> SEQUENCE: 46

```
gtaagttaaa aagaaccaca tgggaaat                                           28
```

<210> SEQ ID NO 47
<211> LENGTH: 23
<212> TYPE: DNA
<213> ORGANISM: Homo sapiens
<400> SEQUENCE: 47

```
ccactcacag gaaacaccca cag                                                23
```

<210> SEQ ID NO 48
<211> LENGTH: 24
<212> TYPE: DNA
<213> ORGANISM: Homo sapiens -continued

<400> SEQUENCE: 48
catgactttg tgtgaatgta cacc                                    24

<210> SEQ ID NO 49
<211> LENGTH: 56
<212> TYPE: DNA
<213> ORGANISM: Homo sapiens

<400> SEQUENCE: 49
tgtgacctca cccctcagga cagttttgaa ctggttgctt tcttttatt gtttag   56

<210> SEQ ID NO 50
<211> LENGTH: 94
<212> TYPE: DNA
<213> ORGANISM: Homo sapiens

<400> SEQUENCE: 50
atcgtctggt agaatcaact tccttgagaa aagccataga aacagtgtat gcagcctatt   60
tgcccaaaaa cacacaccca ttcctgtacc tcag                             94

<210> SEQ ID NO 51
<211> LENGTH: 41
<212> TYPE: DNA
<213> ORGANISM: Homo sapiens

<400> SEQUENCE: 51
gtaatgtagc accaaactcc tcaaccaaga ctcacaagga a                   41

<210> SEQ ID NO 52
<211> LENGTH: 24
<212> TYPE: DNA
<213> ORGANISM: Homo sapiens

<400> SEQUENCE: 52
cagatgttct atcaggctct cctc                                    24

<210> SEQ ID NO 53
<211> LENGTH: 20
<212> TYPE: DNA
<213> ORGANISM: Homo sapiens

<400> SEQUENCE: 53 gggcttttc tccccctccc                                          20

<210> SEQ ID NO 54
<211> LENGTH: 39
<212> TYPE: DNA
<213> ORGANISM: Homo sapiens

<400> SEQUENCE: 54
actatctaag gtaattgttc tctcttattt tcctgacag                     39

<210> SEQ ID NO 55
<211> LENGTH: 154
<212> TYPE: DNA
<213> ORGANISM: Homo sapiens

<400> SEQUENCE: 55
tttagaaatc agtccccaga atgtggatgt taatgtgcac cccacaaagc atgaagttca   60
cttcctgcac gaggagagca tcctggagcg ggtgcagcag cacatcgaga gcaagctcct  120

```
gggctccaat tcctccagga tgtacttcac ccag                         154
```

<210> SEQ ID NO 56
<211> LENGTH: 58
<212> TYPE: DNA
<213> ORGANISM: Homo sapiens

<400> SEQUENCE: 56

```
gtcagggcgc ttctcatcca gctacttctc tggggccttt gaaatgtgcc cggccaga    58
```

<210> SEQ ID NO 57
<211> LENGTH: 18
<212> TYPE: DNA
<213> ORGANISM: Homo sapiens

<400> SEQUENCE: 57

```
cgtgagagcc cagatttt                                           18
```

<210> SEQ ID NO 58
<211> LENGTH: 19
<212> TYPE: DNA
<213> ORGANISM: Homo sapiens

<400> SEQUENCE: 58

```
aattatacct catactagc                                          19
```

<210> SEQ ID NO 59
<211> LENGTH: 116
<212> TYPE: DNA
<213> ORGANISM: Homo sapiens

<400> SEQUENCE: 59

```
ttctttctta gtactgctcc atttggggac ctgtatatct atacttctta ttctgagtct    60
ctccactata tatatatata tatatatatt ttttttttttt tttttttta atacag       116
```

<210> SEQ ID NO 60
<211> LENGTH: 371
<212> TYPE: DNA
<213> ORGANISM: Homo sapiens

<400> SEQUENCE: 60

```
actttgctac caggacttgc tggcccctct ggggagatgg ttaaatccac aacaagtctg    60
acctcgtctt ctacttctgg aagtagtgat aaggtctatg cccaccagat ggttcgtaca   120
gattcccggg aacagaagct tgatgcattt ctgcagcctc tgagcaaacc cctgtccagt   180
cagccccagg ccattgtcac agaggataag acagatattt ctagtggcag ggctaggcag   240
caagatgagg agatgcttga actcccagcc cctgctgaag tggctgccaa aaatcagagc   300 ttggagggg atacaacaaa ggggacttca gaaatgtcag agaagagagg acctacttcc   360
agcaacccca g                                                  371
```

<210> SEQ ID NO 61
<211> LENGTH: 29
<212> TYPE: DNA
<213> ORGANISM: Homo sapiens

<400> SEQUENCE: 61

```
gtatggcctt ttgggaaaag tacagccta                               29
```

<210> SEQ ID NO 62
<211> LENGTH: 23

```
<212> TYPE: DNA
<213> ORGANISM: Homo sapiens

<400> SEQUENCE: 62
cctcctttat tctgtaataa aac                                           23

<210> SEQ ID NO 63
<211> LENGTH: 20
<212> TYPE: DNA
<213> ORGANISM: Homo sapiens

<400> SEQUENCE: 63
tgcaacccac aaaatttggc                                               20

<210> SEQ ID NO 64
<211> LENGTH: 53
<212> TYPE: DNA
<213> ORGANISM: Homo sapiens

<400> SEQUENCE: 64 taagttttaaa aacaagaata ataatgatct gcacttcctt ttcttcattg cag         53

<210> SEQ ID NO 65
<211> LENGTH: 149
<212> TYPE: DNA
<213> ORGANISM: Homo sapiens

<400> SEQUENCE: 65
aaagagacat cgggaagatt ctgatgtgga aatggtggaa gatgattccc gaaaggaaat    60
gactgcagct tgtaccccccc ggagaaggat cattaacctc actagtgttt tgagtctcca  120
ggaagaaatt aatgagcagg gacatgagg                                    149

<210> SEQ ID NO 66
<211> LENGTH: 50
<212> TYPE: DNA
<213> ORGANISM: Homo sapiens

<400> SEQUENCE: 66
gtacgtaaac gctgtggcct gcctgggatg catagggcct caactgccaa               50

<210> SEQ ID NO 67
<211> LENGTH: 20
<212> TYPE: DNA
<213> ORGANISM: Homo sapiens

<400> SEQUENCE: 67
ggttttggaa atggagaaag                                               20

<210> SEQ ID NO 68
<211> LENGTH: 18
<212> TYPE: DNA
<213> ORGANISM: Homo sapiens

<400> SEQUENCE: 68
tggtgtctct agttctgg                                                 18

<210> SEQ ID NO 69
<211> LENGTH: 82
<212> TYPE: DNA
<213> ORGANISM: Homo sapiens

<400> SEQUENCE: 69
```
tgcctggtgc tttggtcaat gaagtggggt tggtaggatt ctattactta cctgtttttt    60 ggtttttattt tttgttttgc ag                                             82

<210> SEQ ID NO 70
<211> LENGTH: 109
<212> TYPE: DNA
<213> ORGANISM: Homo sapiens

<400> SEQUENCE: 70
ttctccggga gatgttgcat aaccactcct tcgtgggctg tgtgaatcct cagtgggcct    60
tggcacagca tcaaaccaag ttataccttc tcaacaccac caagcttag               109

<210> SEQ ID NO 71
<211> LENGTH: 25
<212> TYPE: DNA
<213> ORGANISM: Homo sapiens

<400> SEQUENCE: 71
gtaaatcagc tgagtgtgtg aacaa                                           25

<210> SEQ ID NO 72
<211> LENGTH: 20
<212> TYPE: DNA
<213> ORGANISM: Homo sapiens

<400> SEQUENCE: 72
gcagagctac tacaacaatg                                                 20

<210> SEQ ID NO 73
<211> LENGTH: 18
<212> TYPE: DNA
<213> ORGANISM: Homo sapiens

<400> SEQUENCE: 73
cccatttgtc ccaactgg                                                   18

<210> SEQ ID NO 74
<211> LENGTH: 57
<212> TYPE: DNA
<213> ORGANISM: Homo sapiens

<400> SEQUENCE: 74
ttgtatctca agcatgaatt cagcttttcc ttaaagtcac ttcatttta ttttcag         57

<210> SEQ ID NO 75
<211> LENGTH: 64
<212> TYPE: DNA
<213> ORGANISM: Homo sapiens

<400> SEQUENCE: 75
tgaagaactg ttctaccaga tactcattta tgattttgcc aatttggtg ttctcaggtt      60 atcg                                                                  64

<210> SEQ ID NO 76
<211> LENGTH: 23
<212> TYPE: DNA
<213> ORGANISM: Homo sapiens

<400> SEQUENCE: 76
gtaagtttag atccttttca ctt                                             23

```
<210> SEQ ID NO 77
<211> LENGTH: 19
<212> TYPE: DNA
<213> ORGANISM: Homo sapiens

<400> SEQUENCE: 77
ctgacatttc aactgaccg                                              19

<210> SEQ ID NO 78
<211> LENGTH: 22
<212> TYPE: DNA
<213> ORGANISM: Homo sapiens

<400> SEQUENCE: 78
catttggatg ctccgttaaa gc                                          22

<210> SEQ ID NO 79
<211> LENGTH: 30
<212> TYPE: DNA
<213> ORGANISM: Homo sapiens

<400> SEQUENCE: 79
ttgctccttc atgttcttgc ttcttcctag                                  30

<210> SEQ ID NO 80
<211> LENGTH: 165
<212> TYPE: DNA
<213> ORGANISM: Homo sapiens

<400> SEQUENCE: 80
gagccagcac cgctctttga ccttgccatg cttgccttag atagtccaga gagtggctgg   60
acagaggaag atggtcccaa agaaggactt gctgaataca ttgttgagtt tctgaagaag  120
aaggctgaga tgcttgcaga ctatttctct ttggaaattg atgag                  165

<210> SEQ ID NO 81
<211> LENGTH: 36
<212> TYPE: DNA
<213> ORGANISM: Homo sapiens

<400> SEQUENCE: 81
gtgtgacagc cattcttata cttctgttgt attctc                           36

<210> SEQ ID NO 82
<211> LENGTH: 23
<212> TYPE: DNA
<213> ORGANISM: Homo sapiens

<400> SEQUENCE: 82
caaataaaat ttccagccgg gtg                                         23

<210> SEQ ID NO 83
<211> LENGTH: 22
<212> TYPE: DNA
<213> ORGANISM: Homo sapiens

<400> SEQUENCE: 83
ggaaaggcac tggagaaatg gg                                          22

<210> SEQ ID NO 84
<211> LENGTH: 59
<212> TYPE: DNA
<213> ORGANISM: Homo sapiens
```

```
<400> SEQUENCE: 84
atttgtttaa actatgacag cattatttct tgttcccttg tccttttccc tgcaagcag       59

<210> SEQ ID NO 85
<211> LENGTH: 93
<212> TYPE: DNA
<213> ORGANISM: Homo sapiens

<400> SEQUENCE: 85
gaagggaacc tgattggatt accccttctg attgacaact atgtgccccc tttggaggga      60
ctgcctatct tcattcttcg actagccact gag                                   93

<210> SEQ ID NO 86
<211> LENGTH: 29
<212> TYPE: DNA
<213> ORGANISM: Homo sapiens

<400> SEQUENCE: 86
gtcagtgatc aagcagatac taagcattt                                        29

<210> SEQ ID NO 87
<211> LENGTH: 25
<212> TYPE: DNA
<213> ORGANISM: Homo sapiens

<400> SEQUENCE: 87
cggtacatgc atgtgtgctg gaggg                                            25

<210> SEQ ID NO 88
<211> LENGTH: 20
<212> TYPE: DNA
<213> ORGANISM: Homo sapiens

<400> SEQUENCE: 88
taagtagtct gtgatctccg                                                  20

<210> SEQ ID NO 89
<211> LENGTH: 60
<212> TYPE: DNA
<213> ORGANISM: Homo sapiens

<400> SEQUENCE: 89
tttagaatga gaatgtttaa attcgtacct attttgaggt attgaatttc tttggaccag       60

<210> SEQ ID NO 90
<211> LENGTH: 114
<212> TYPE: DNA
<213> ORGANISM: Homo sapiens

<400> SEQUENCE: 90
gtgaattggg acgaagaaaa ggaatgtttt gaaagcctca gtaaagaatg cgctatgttc       60
tattccatcc ggaagcagta catatctgag gagtcgaccc tctcaggcca gcag            114

<210> SEQ ID NO 91
<211> LENGTH: 35
<212> TYPE: DNA
<213> ORGANISM: Homo sapiens

<400> SEQUENCE: 91
gtacagtggt gatgcacact ggcaccccag gacta                                 35
```

```
<210> SEQ ID NO 92
<211> LENGTH: 18
<212> TYPE: DNA
<213> ORGANISM: Homo sapiens

<400> SEQUENCE: 92
ggacaggacc tcatacat                                                  18

<210> SEQ ID NO 93
<211> LENGTH: 18
<212> TYPE: DNA
<213> ORGANISM: Homo sapiens

<400> SEQUENCE: 93
gacaccagtg tatgttgg                                                  18

<210> SEQ ID NO 94
<211> LENGTH: 42
<212> TYPE: DNA
<213> ORGANISM: Homo sapiens

<400> SEQUENCE: 94
gatgcaaaca gggaggctta tgacatctaa tgtgttttcc ag                       42

<210> SEQ ID NO 95
<211> LENGTH: 168
<212> TYPE: DNA
<213> ORGANISM: Homo sapiens

<400> SEQUENCE: 95
agtgaagtgc ctggctccat tccaaactcc tggaagtgga ctgtggaaca cattgtctat    60
aaagccttgc gctcacacat tctgcctcct aaacatttca cagaagatgg aaatatcctg   120
cagcttgcta acctgcctga tctatacaaa gtctttgaga ggtgttaa                168

<210> SEQ ID NO 96
<211> LENGTH: 21
<212> TYPE: DNA
<213> ORGANISM: Homo sapiens

<400> SEQUENCE: 96
atatggttat ttatgcactg t                                              21

<210> SEQ ID NO 97
<211> LENGTH: 20
<212> TYPE: DNA
<213> ORGANISM: Homo sapiens

<400> SEQUENCE: 97
gggatgtgtt cttctttctc                                                20

<210> SEQ ID NO 98
<211> LENGTH: 60
<212> TYPE: DNA
<213> ORGANISM: Homo sapiens

<400> SEQUENCE: 98
tgtattccga tacaaagtgt tgtatcaaag tgtgatatac aaagtgtacc aacataagtg    60

<210> SEQ ID NO 99
<211> LENGTH: 31
<212> TYPE: DNA
<213> ORGANISM: Homo sapiens
```

```
<400> SEQUENCE: 99
ggcgggaaac agcttagtgg gtgtggggtc g                              31

<210> SEQ ID NO 100
<211> LENGTH: 20
<212> TYPE: DNA
<213> ORGANISM: Homo sapiens

<400> SEQUENCE: 100
cgcattttct tcaaccagga                                           20

<210> SEQ ID NO 101
<211> LENGTH: 17
<212> TYPE: DNA
<213> ORGANISM: Homo sapiens

<400> SEQUENCE: 101
ggtgaggagg tttcgac                                              17

<210> SEQ ID NO 102
<211> LENGTH: 211
<212> TYPE: DNA
<213> ORGANISM: Homo sapiens

<400> SEQUENCE: 102
atggcggtgc agccgaagga gacgctgcag ttggagagcg cggccgaggt cggcttcgtg    60
cgcttctttc agggcatgcc ggagaagccg accaccacag tgcgcctttt cgaccggggc   120
gacttctata cggcgcacgg cgaggacgcg ctgctggccg cccgggaggt gttcaagacc   180 caggggtga tcaagtacat ggggccggca g                                  211

<210> SEQ ID NO 103
<211> LENGTH: 14
<212> TYPE: DNA
<213> ORGANISM: Homo sapiens

<400> SEQUENCE: 103
gtgagggccg ggac                                                 14

<210> SEQ ID NO 104
<211> LENGTH: 17
<212> TYPE: DNA
<213> ORGANISM: Homo sapiens

<400> SEQUENCE: 104
ggcgcgtgct ggggagg                                              17

<210> SEQ ID NO 105
<211> LENGTH: 21
<212> TYPE: DNA
<213> ORGANISM: Homo sapiens

<400> SEQUENCE: 105
gtccagctaa tacagtgctt g                                         21

<210> SEQ ID NO 106
<211> LENGTH: 46
<212> TYPE: DNA
<213> ORGANISM: Homo sapiens

<400> SEQUENCE: 106
aacatgtaat atctcaaatc tgtaatgtac ttttttttt tttaag               46
```

<210> SEQ ID NO 107
<211> LENGTH: 155
<212> TYPE: DNA
<213> ORGANISM: Homo sapiens

<400> SEQUENCE: 107

```
gagcaaagaa tctgcagagt gttgtgctta gtaaaatgaa ttttgaatct tttgtaaaag      60
atcttcttct ggttcgtcag tatagagttg aagtttataa gaatagagct ggaaataagg     120
catccaagga gaatgattgg tatttggcat ataag                                155
```

<210> SEQ ID NO 108
<211> LENGTH: 33
<212> TYPE: DNA
<213> ORGANISM: Homo sapiens

<400> SEQUENCE: 108

```
gtaattatct tcctttttaa tttacttatt ttt                                   33
```

<210> SEQ ID NO 109
<211> LENGTH: 25
<212> TYPE: DNA
<213> ORGANISM: Homo sapiens

<400> SEQUENCE: 109

```
ttaagagtag aaaaataaaa atgtg                                            25
```

<210> SEQ ID NO 110
<211> LENGTH: 32
<212> TYPE: DNA
<213> ORGANISM: Homo sapiens

<400> SEQUENCE: 110

```
attaataagg ttcatagagt ttggattttt cc                                    32
```

<210> SEQ ID NO 111
<211> LENGTH: 26
<212> TYPE: DNA
<213> ORGANISM: Homo sapiens

<400> SEQUENCE: 111

```
ttataaaatt ttaaagtatg ttcaag                                           26
```

<210> SEQ ID NO 112
<211> LENGTH: 36
<212> TYPE: DNA
<213> ORGANISM: Homo sapiens

<400> SEQUENCE: 112

```
agtttgttaa attttaaaa ttttatttt acttag                                  36
```

<210> SEQ ID NO 113
<211> LENGTH: 279
<212> TYPE: DNA
<213> ORGANISM: Homo sapiens

<400> SEQUENCE: 113

```
gcttctcctg gcaatctctc tcagtttgaa gacattctct ttggtaacaa tgatatgtca      60
gcttccattg gtgttgtggg tgttaaaatg tccgcagttg atggccagag acaggttgga     120
gttgggtatg tggattccat acagaggaaa ctaggactgt gtgaattccc tgataatgat     180
```

```
cagttctcca atcttgaggc tctcctcatc cagattggac caaaggaatg tgttttaccc    240
ggaggagaga ctgctggaga catggggaaa ctgagacag                            279
```

<210> SEQ ID NO 114
<211> LENGTH: 23
<212> TYPE: DNA
<213> ORGANISM: Homo sapiens

<400> SEQUENCE: 114

```
gtaagcaaat tgagtctagt gat                                             23
```

<210> SEQ ID NO 115
<211> LENGTH: 25
<212> TYPE: DNA
<213> ORGANISM: Homo sapiens

<400> SEQUENCE: 115

```
agaggagatt ccaggcctag gaaag                                           25
```

<210> SEQ ID NO 116
<211> LENGTH: 21
<212> TYPE: DNA
<213> ORGANISM: Homo sapiens

<400> SEQUENCE: 116

```
tctttaattg acatgatact g                                               21
```

<210> SEQ ID NO 117
<211> LENGTH: 24
<212> TYPE: DNA
<213> ORGANISM: Homo sapiens

<400> SEQUENCE: 117

```
tttttgcttt tcttattcct tttc                                            24
```

<210> SEQ ID NO 118
<211> LENGTH: 33
<212> TYPE: DNA
<213> ORGANISM: Homo sapiens

<400> SEQUENCE: 118

```
tcatagtagt ttaaactatt tctttcaaaa tag                                  33
```

<210> SEQ ID NO 119
<211> LENGTH: 147
<212> TYPE: DNA
<213> ORGANISM: Homo sapiens

<400> SEQUENCE: 119

```
ataattcaaa gaggaggaat tctgatcaca gaaagaaaaa aagctgactt ttccacaaaa    60
gacatttatc aggacctcaa ccggttgttg aaaggcaaaa agggagagca gatgaatagt   120
gctgtattgc cagaaatgga gaatcag                                        147
```

<210> SEQ ID NO 120
<211> LENGTH: 85
<212> TYPE: DNA
<213> ORGANISM: Homo sapiens

<400> SEQUENCE: 120

```
gtacatggat tataaatgtg aattacaata tatataatgt aaatatgtaa tatataataa    60
ataatatgta aactatagtg acttt                                           85
```

<210> SEQ ID NO 121
<211> LENGTH: 20
<212> TYPE: DNA
<213> ORGANISM: Homo sapiens

<400> SEQUENCE: 121
ttagaaggat atttctgtca                                         20

<210> SEQ ID NO 122
<211> LENGTH: 10
<212> TYPE: DNA
<213> ORGANISM: Homo sapiens

<400> SEQUENCE: 122
actggcacca                                                    10

<210> SEQ ID NO 123
<211> LENGTH: 24
<212> TYPE: DNA
<213> ORGANISM: Homo sapiens

<400> SEQUENCE: 123
gtggtataga aatcttcgat tttt                                    24

<210> SEQ ID NO 124
<211> LENGTH: 16
<212> TYPE: DNA
<213> ORGANISM: Homo sapiens

<400> SEQUENCE: 124
aaattcttaa ttttag                                             16

<210> SEQ ID NO 125
<211> LENGTH: 150
<212> TYPE: DNA
<213> ORGANISM: Homo sapiens

<400> SEQUENCE: 125
gttgcagttt catcactgtc tgcggtaatc aagtttttag aactcttatc agatgattcc    60
aactttggac agtttgaact gactactttt gacttcagcc agtatatgaa attggatatt   120
gcagcagtca gagcccttaa ccttttcag                                     150

<210> SEQ ID NO 126
<211> LENGTH: 23
<212> TYPE: DNA
<213> ORGANISM: Homo sapiens

<400> SEQUENCE: 126
gtaaaaaaaa aaaaaaaaaa aaa                                     23

<210> SEQ ID NO 127
<211> LENGTH: 22
<212> TYPE: DNA
<213> ORGANISM: Homo sapiens

<400> SEQUENCE: 127 aaagggtta aaaatgttga tt                                       22

<210> SEQ ID NO 128
<211> LENGTH: 13
<212> TYPE: DNA

```
<213> ORGANISM: Homo sapiens

<400> SEQUENCE: 128
ttaaaaaatg ttt                                                          13

<210> SEQ ID NO 129
<211> LENGTH: 23
<212> TYPE: DNA
<213> ORGANISM: Homo sapiens

<400> SEQUENCE: 129
cattgacata tactgaagaa gct                                               23

<210> SEQ ID NO 130
<211> LENGTH: 27
<212> TYPE: DNA
<213> ORGANISM: Homo sapiens

<400> SEQUENCE: 130 tataaggag ctaaatatt tggaaat                                             27

<210> SEQ ID NO 131
<211> LENGTH: 43
<212> TYPE: DNA
<213> ORGANISM: Homo sapiens

<400> SEQUENCE: 131
attatacttg gattagataa ctagctttaa atgggtgtat ttt                         43

<210> SEQ ID NO 132
<211> LENGTH: 22
<212> TYPE: DNA
<213> ORGANISM: Homo sapiens

<400> SEQUENCE: 132
ttcactaatg agcttgccat tc                                                22

<210> SEQ ID NO 133
<211> LENGTH: 26
<212> TYPE: DNA
<213> ORGANISM: Homo sapiens

<400> SEQUENCE: 133
tttctatttt attttttgtt tactag                                            26

<210> SEQ ID NO 134
<211> LENGTH: 134
<212> TYPE: DNA
<213> ORGANISM: Homo sapiens

<400> SEQUENCE: 134
ggttctgttg aagataccac tggctctcag tctctggctg ccttgctgaa taagtgtaaa       60 accccctcaag gacaaagact tgttaaccag tggattaagc agcctctcat ggataagaac     120
agaatagagg agag                                                        134

<210> SEQ ID NO 135
<211> LENGTH: 44
<212> TYPE: DNA
<213> ORGANISM: Homo sapiens

<400> SEQUENCE: 135
gtatgttatt agtttatact ttcgttagtt ttatgtaacc tgca                        44
```

<210> SEQ ID NO 136
<211> LENGTH: 20
<212> TYPE: DNA
<213> ORGANISM: Homo sapiens

<400> SEQUENCE: 136
gttacccaca tgattatacc                                              20

<210> SEQ ID NO 137
<211> LENGTH: 20
<212> TYPE: DNA
<213> ORGANISM: Homo sapiens

<400> SEQUENCE: 137
cttacgtgct tagttgataa                                              20

<210> SEQ ID NO 138
<211> LENGTH: 53
<212> TYPE: DNA
<213> ORGANISM: Homo sapiens

<400> SEQUENCE: 138
attttaattt tatactaaaa tattttacat taattcaagt taatttattt cag          53

<210> SEQ ID NO 139
<211> LENGTH: 200
<212> TYPE: DNA
<213> ORGANISM: Homo sapiens

<400> SEQUENCE: 139
attgaattta gtggaagctt ttgtagaaga tgcagaattg aggcagactt tacaagaaga    60
tttacttcgt cgattcccag atcttaaccg acttgccaag aagtttcaaa gacaagcagc   120
aaacttacaa gattgttacc gactctatca gggtataaat caactaccta atgttataca   180
ggctctggaa aaacatgaag                                              200

<210> SEQ ID NO 140
<211> LENGTH: 24
<212> TYPE: DNA
<213> ORGANISM: Homo sapiens

<400> SEQUENCE: 140
gtaacaagtg attttgtttt tttg                                         24

<210> SEQ ID NO 141
<211> LENGTH: 24
<212> TYPE: DNA
<213> ORGANISM: Homo sapiens

<400> SEQUENCE: 141
ttttccttca actcatacaa tata                                         24

<210> SEQ ID NO 142
<211> LENGTH: 26
<212> TYPE: DNA
<213> ORGANISM: Homo sapiens

<400> SEQUENCE: 142
tttgtattct gtaaaatgag atcttt                                       26

<210> SEQ ID NO 143

```
<211> LENGTH: 30
<212> TYPE: DNA
<213> ORGANISM: Homo sapiens

<400> SEQUENCE: 143
ttatttgttt gttttactac tttcttttag                              30

<210> SEQ ID NO 144
<211> LENGTH: 110
<212> TYPE: DNA
<213> ORGANISM: Homo sapiens

<400> SEQUENCE: 144
gaaaacacca gaaattattg ttggcagttt ttgtgactcc tcttactgat cttcgttctg    60
acttctccaa gtttcaggaa atgatagaaa caactttaga tatggatcag              110

<210> SEQ ID NO 145
<211> LENGTH: 26
<212> TYPE: DNA
<213> ORGANISM: Homo sapiens

<400> SEQUENCE: 145
gtatgcaata tactttttaa tttaag                                   26

<210> SEQ ID NO 146
<211> LENGTH: 25
<212> TYPE: DNA
<213> ORGANISM: Homo sapiens

<400> SEQUENCE: 146
cagtagttat ttttaaaaag caaag                                    25

<210> SEQ ID NO 147
<211> LENGTH: 23
<212> TYPE: DNA
<213> ORGANISM: Homo sapiens

<400> SEQUENCE: 147
ctttacccat tatttatagg att                                      23

<210> SEQ ID NO 148
<211> LENGTH: 23
<212> TYPE: DNA
<213> ORGANISM: Homo sapiens

<400> SEQUENCE: 148
ttgtcacttt gttctgtttg cag                                      23

<210> SEQ ID NO 149
<211> LENGTH: 124
<212> TYPE: DNA
<213> ORGANISM: Homo sapiens

<400> SEQUENCE: 149
gtggaaaacc atgaattcct tgtaaaacct tcatttgatc ctaatctcag tgaattaaga    60
gaaataatga atgacttgga aaagaagatg cagtcaacat taataagtgc agccagagat   120
cttg                                                          124

<210> SEQ ID NO 150
<211> LENGTH: 20
<212> TYPE: DNA
<213> ORGANISM: Homo sapiens
```

```
<400> SEQUENCE: 150
gtaagaatgg gtcattggag                                              20

<210> SEQ ID NO 151
<211> LENGTH: 23
<212> TYPE: DNA
<213> ORGANISM: Homo sapiens

<400> SEQUENCE: 151
gttggaataa ttcttttgtc tat                                          23

<210> SEQ ID NO 152
<211> LENGTH: 25
<212> TYPE: DNA
<213> ORGANISM: Homo sapiens

<400> SEQUENCE: 152
tagtaggtat ttatggaata ctttt                                        25

<210> SEQ ID NO 153
<211> LENGTH: 22
<212> TYPE: DNA
<213> ORGANISM: Homo sapiens

<400> SEQUENCE: 153
tcttttcttc ttgtttatca ag                                           22

<210> SEQ ID NO 154
<211> LENGTH: 151
<212> TYPE: DNA
<213> ORGANISM: Homo sapiens

<400> SEQUENCE: 154
gcttggaccc tggcaaacag attaaactgg attccagtgc acagtttgga tattactttc   60
gtgtaacctg taaggaagaa aaagtccttc gtaacaataa aaactttagt actgtagata  120
tccagaagaa tggtgttaaa tttaccaaca g                                 151

<210> SEQ ID NO 155
<211> LENGTH: 36
<212> TYPE: DNA
<213> ORGANISM: Homo sapiens

<400> SEQUENCE: 155
gtttgtaagt cattattata tttttaaccc tttatt                            36

<210> SEQ ID NO 156
<211> LENGTH: 21
<212> TYPE: DNA
<213> ORGANISM: Homo sapiens

<400> SEQUENCE: 156
aattccctaa atgctctaac a                                            21

<210> SEQ ID NO 157
<211> LENGTH: 21
<212> TYPE: DNA
<213> ORGANISM: Homo sapiens

<400> SEQUENCE: 157
cattgcttct agtacacatt t                                            21
```

```
<210> SEQ ID NO 158
<211> LENGTH: 36
<212> TYPE: DNA
<213> ORGANISM: Homo sapiens

<400> SEQUENCE: 158
taatattttt aataaaactg ttatttcgat ttgcag                              36

<210> SEQ ID NO 159
<211> LENGTH: 98
<212> TYPE: DNA
<213> ORGANISM: Homo sapiens

<400> SEQUENCE: 159
caaattgact tctttaaatg aagagtatac caaaaataaa acagaatatg aagaagccca    60
ggatgccatt gttaaagaaa ttgtcaatat ttcttcag                            98

<210> SEQ ID NO 160
<211> LENGTH: 19
<212> TYPE: DNA
<213> ORGANISM: Homo sapiens

<400> SEQUENCE: 160
gtaaacttaa tagaactaa                                                 19

<210> SEQ ID NO 161
<211> LENGTH: 21
<212> TYPE: DNA
<213> ORGANISM: Homo sapiens

<400> SEQUENCE: 161
taatgttctg aatgtcacct g                                              21

<210> SEQ ID NO 162
<211> LENGTH: 21
<212> TYPE: DNA
<213> ORGANISM: Homo sapiens

<400> SEQUENCE: 162
tcagtattcc tgtgtacatt t                                              21

<210> SEQ ID NO 163
<211> LENGTH: 21
<212> TYPE: DNA
<213> ORGANISM: Homo sapiens

<400> SEQUENCE: 163
tctgttttta tttttataca g                                              21

<210> SEQ ID NO 164
<211> LENGTH: 246
<212> TYPE: DNA
<213> ORGANISM: Homo sapiens

<400> SEQUENCE: 164
gctatgtaga accaatgcag acactcaatg atgtgttagc tcagctagat gctgttgtca    60
gctttgctca cgtgtcaaat ggagcacctg ttccatatgt acgaccagcc attttggaga   120
aaggacaagg aagaattata ttaaaagcat ccaggcatgc ttgtgttgaa gttcaagatg   180
aaattgcatt tattcctaat gacgtatact ttgaaaaaga taaacagatg ttccacatca   240
ttactg                                                              246
```

<210> SEQ ID NO 165
<211> LENGTH: 16
<212> TYPE: DNA
<213> ORGANISM: Homo sapiens

<400> SEQUENCE: 165
gtaaaaaacc tggttt                                                         16

<210> SEQ ID NO 166
<211> LENGTH: 19
<212> TYPE: DNA
<213> ORGANISM: Homo sapiens

<400> SEQUENCE: 166
ttgggctttg tggggtaa                                                       19

<210> SEQ ID NO 167
<211> LENGTH: 19
<212> TYPE: DNA
<213> ORGANISM: Homo sapiens

<400> SEQUENCE: 167
cgattaatca tcagtgtac                                                      19

<210> SEQ ID NO 168
<211> LENGTH: 78
<212> TYPE: DNA
<213> ORGANISM: Homo sapiens

<400> SEQUENCE: 168
agtttaggac taacaatcca tttattagta gcagaaagaa gtttaaaatc ttgctttctg         60
atataatttg ttttgtag                                                       78

<210> SEQ ID NO 169
<211> LENGTH: 205
<212> TYPE: DNA
<213> ORGANISM: Homo sapiens

<400> SEQUENCE: 169
gccccaatat gggaggtaaa tcaacatata ttcgacaaac tggggtgata gtactcatgg         60
cccaaattgg gtgttttgtg ccatgtgagt cagcagaagt gtccattgtg gactgcatct        120
tagcccgagt aggggctggt gacagtcaat tgaaaggagt ctccacgttc atggctgaaa        180
tgttggaaac tgcttctatc ctcag                                              205

<210> SEQ ID NO 170
<211> LENGTH: 23
<212> TYPE: DNA
<213> ORGANISM: Homo sapiens

<400> SEQUENCE: 170
gtaagtgcat ctcctagtcc ctt                                                 23

<210> SEQ ID NO 171
<211> LENGTH: 23
<212> TYPE: DNA
<213> ORGANISM: Homo sapiens

<400> SEQUENCE: 171
gaagatagaa atgtatgtct ctg                                                 23

<210> SEQ ID NO 172
<211> LENGTH: 21
<212> TYPE: DNA
<213> ORGANISM: Homo sapiens

<400> SEQUENCE: 172
ccacatttta tgtgatggga a                                              21

<210> SEQ ID NO 173
<211> LENGTH: 24
<212> TYPE: DNA
<213> ORGANISM: Homo sapiens

<400> SEQUENCE: 173
atttcatgta attatgtgct tcag                                           24

<210> SEQ ID NO 174
<211> LENGTH: 248
<212> TYPE: DNA
<213> ORGANISM: Homo sapiens

<400> SEQUENCE: 174
gtctgcaacc aaagattcat taataatcat agatgaattg ggaagaggaa cttctaccta    60
cgatggattt gggttagcat gggctatatc agaatacatt gcaacaaaga ttggtgcttt   120
ttgcatgttt gcaacccatt ttcatgaact tactgccttg gccaatcaga taccaactgt   180
taataatcta catgtcacag cactcaccac tgaagagacc ttaactatgc tttatcaggt   240
gaagaaag                                                            248

<210> SEQ ID NO 175
<211> LENGTH: 56
<212> TYPE: DNA
<213> ORGANISM: Homo sapiens

<400> SEQUENCE: 175
gtatgtacta ttggagtact ctaaattcag aacttggtaa tgggaaactt actacc        56

<210> SEQ ID NO 176
<211> LENGTH: 19
<212> TYPE: DNA
<213> ORGANISM: Homo sapiens

<400> SEQUENCE: 176
cttctcatgc tgtcccctc                                                 19

<210> SEQ ID NO 177
<211> LENGTH: 23
<212> TYPE: DNA
<213> ORGANISM: Homo sapiens

<400> SEQUENCE: 177
acgcttcccc aaatttctta tag                                            23

<210> SEQ ID NO 178
<211> LENGTH: 176
<212> TYPE: DNA
<213> ORGANISM: Homo sapiens

<400> SEQUENCE: 178
gtgtctgtga tcaaagtttt gggattcatg ttgcagagct tgctaatttc cctaagcatg    60
taatagagtg tgctaaacag aaagccctgg aacttgagga gtttcagtat attggagaat   120

```
cgcaaggata tgatatcatg gaaccagcag caaagaagtg ctatctggaa agagag        176

<210> SEQ ID NO 179
<211> LENGTH: 17
<212> TYPE: DNA
<213> ORGANISM: Homo sapiens

<400> SEQUENCE: 179
gtttgtcagt ttgtttt                                                   17

<210> SEQ ID NO 180
<211> LENGTH: 21
<212> TYPE: DNA
<213> ORGANISM: Homo sapiens

<400> SEQUENCE: 180
catagtttaa cttagcttct c                                              21

<210> SEQ ID NO 181
<211> LENGTH: 21
<212> TYPE: DNA
<213> ORGANISM: Homo sapiens

<400> SEQUENCE: 181
attactcatg ggacattcac a                                              21

<210> SEQ ID NO 182
<211> LENGTH: 10
<212> TYPE: DNA
<213> ORGANISM: Homo sapiens

<400> SEQUENCE: 182
tgtgtttcag                                                           10

<210> SEQ ID NO 183
<211> LENGTH: 171
<212> TYPE: DNA
<213> ORGANISM: Homo sapiens

<400> SEQUENCE: 183
caaggtgaaa aaattattca ggagttcctg tccaaggtga acaaatgcc ctttactgaa     60 atgtcagaag aaaacatcac aataaagtta aaacagctaa aagctgaagt aatagcaaag   120
aataatagct ttgtaaatga aatcatttca cgaataaaag ttactacgtg a            171

<210> SEQ ID NO 184
<211> LENGTH: 20
<212> TYPE: DNA
<213> ORGANISM: Homo sapiens

<400> SEQUENCE: 184
atcccagtaa tggaatgaag                                                20

<210> SEQ ID NO 185
<211> LENGTH: 37
<212> TYPE: DNA
<213> ORGANISM: Artificial Sequence
<220> FEATURE:
<223> OTHER INFORMATION: Description of Artificial Sequence: Synthetic

<400> SEQUENCE: 185
tgtaaaacga cggccagtct gaggtgattg gctgaag                             37
```

<210> SEQ ID NO 186
<211> LENGTH: 38
<212> TYPE: DNA
<213> ORGANISM: Artificial Sequence
<220> FEATURE:
<223> OTHER INFORMATION: Description of Artificial Sequence: Synthetic

<400> SEQUENCE: 186
ggaaacagct atgaccatgc cgttaagtcg tagcccctt                    38

<210> SEQ ID NO 187
<211> LENGTH: 37
<212> TYPE: DNA
<213> ORGANISM: Artificial Sequence
<220> FEATURE:
<223> OTHER INFORMATION: Description of Artificial Sequence: Synthetic

<400> SEQUENCE: 187
tgtaaaacga cggccagtcg attaatcatc agtgtac                      37

<210> SEQ ID NO 188
<211> LENGTH: 42
<212> TYPE: DNA
<213> ORGANISM: Artificial Sequence
<220> FEATURE:
<223> OTHER INFORMATION: Description of Artificial Sequence: Synthetic

<400> SEQUENCE: 188
ggaaacagct atgaccatgc agagacatac atttctatct tc                42

<210> SEQ ID NO 189
<211> LENGTH: 38
<212> TYPE: DNA
<213> ORGANISM: Artificial Sequence
<220> FEATURE:
<223> OTHER INFORMATION: Description of Artificial Sequence: Synthetic

<400> SEQUENCE: 189
tgtaaaacga cggccagtcg cattttcttc aaccagga                     38

<210> SEQ ID NO 190
<211> LENGTH: 36
<212> TYPE: DNA
<213> ORGANISM: Artificial Sequence
<220> FEATURE:
<223> OTHER INFORMATION: Description of Artificial Sequence: Synthetic

<400> SEQUENCE: 190
ggaaacagct atgaccatgc ctccccagca cgcgcc                       36

<210> SEQ ID NO 191
<211> LENGTH: 23
<212> TYPE: DNA
<213> ORGANISM: Artificial Sequence
<220> FEATURE:
<223> OTHER INFORMATION: Description of Artificial Sequence: Synthetic

<400> SEQUENCE: 191
ggccattgtc acagaggata aga                                     23

<210> SEQ ID NO 192
<211> LENGTH: 20
<212> TYPE: DNA
<213> ORGANISM: Artificial Sequence -continued

```
<220> FEATURE:
<223> OTHER INFORMATION: Description of Artificial Sequence: Synthetic

<400> SEQUENCE: 192
acacagccca cgaaggagtg                                                  20
```